US008795682B2

(12) United States Patent
Compans et al.

(10) Patent No.: US 8,795,682 B2
(45) Date of Patent: Aug. 5, 2014

(54) VIRUS-LIKE PARTICLES COMPRISING CHIMERIC HUMAN IMMUNODEFICIENCY VIRUS (HIV)/MOUSE MAMMARY TUMOR VIRUS (MMTV) ENVELOPES

(75) Inventors: Richard W. Compans, Atlanta, GA (US); Baozhong Wang, Atlanta, GA (US); Beatrice Hahn, Birmingham, AL (US); Weimin Liu, Hoover, AL (US); Gale Smith, Gaithersburg, MD (US); Peter Pushko, Frederick, MD (US)

(73) Assignees: Emory University, Atlanta, GA (US); The UAB Research Foundation, Birmingham, AL (US); Novavax, Inc., Rockville, MD (US)

( * ) Notice: Subject to any disclaimer, the term of this patent is extended or adjusted under 35 U.S.C. 154(b) by 853 days.

(21) Appl. No.: 12/598,271

(22) PCT Filed: May 2, 2008

(86) PCT No.: PCT/US2008/062516
§ 371 (c)(1),
(2), (4) Date: Mar. 31, 2010

(87) PCT Pub. No.: WO2009/009215
PCT Pub. Date: Jan. 15, 2009

(65) Prior Publication Data
US 2010/0196419 A1      Aug. 5, 2010

Related U.S. Application Data

(60) Provisional application No. 60/927,208, filed on May 2, 2007.

(51) Int. Cl.
*A61K 39/12*          (2006.01)
*A61K 39/21*          (2006.01)
(52) U.S. Cl.
USPC .................. 424/199.1; 424/207.1; 424/208.1
(58) Field of Classification Search
None
See application file for complete search history.

(56) References Cited

U.S. PATENT DOCUMENTS

| 3,817,837 | A  | 6/1974  | Rubenstein et al. |
| 3,850,752 | A  | 11/1974 | Schuurs et al. |
| 3,939,350 | A  | 2/1976  | Kronick et al. |
| 3,996,345 | A  | 12/1976 | Ullman et al. |
| 4,275,149 | A  | 6/1981  | Litman et al. |
| 4,277,437 | A  | 7/1981  | Maggio |
| 4,366,241 | A  | 12/1982 | Tom et al. |
| 4,816,567 | A  | 3/1989  | Cabilly et al. |
| 7,067,134 | B1 | 6/2006  | Kang et al. |
| 2006/0216702 | A1 | 9/2006 | Compans et al. |

OTHER PUBLICATIONS

Deml, L., et al., 1997, Increased incorporation of chimeric human immunodeficiency virus type 1 gp120 proteins into Pr55gag virus-like particles by an Epstein-Barr virus gp220/350-derived transmembrane domain, Virol. 235:10-25.*
Li, Y., et al., 1994, Control of expression, glycosylation, and secretion of HIV-1 gp120 by homologous and heterologous signal sequences, Virol. 204:266-278.*
Liao, H.-X., et al., 2006, A group M consensus envelope glycoprotein induces antibodies that neutralize subsets of subtype B and C HIV-1 primary viruses, Virol. 353:268-282.*
Supplemental European Search Report dated Jun. 15, 2011.
Moreno, et al., "The Membranotropic Regions of the Endo an Ecto Domains of HIV gp41 Envelope Glycoprotein," Biochimica et Biophysica Acta, Biomembranes, Amsterdam, NL, vol. 1758, No. 1, Jan. 1, 2006, pp. 111-123.
Liao, et al., "A Group M Consensus Envelope Glycoprotein Induces Antibodies That Neutralize Subsets of Subtype B and C HIV-1 Primary Viruses," Virology, Academic Press, Orlando, FL vol. 353, No. 2, Sep. 20, 2006, pp. 268-282.
Akira, et al., (2004), "Toll-like receptor signalling.", Nat Rev Immunol, 4(7): 499-511.
Baker et al., (1991), "Structures of bovine and human papillomaviruses. Analysis by cryoelectron microscopy and three-dimensional image reconstruction.", Biophysical Journal, 60(6): 1445-1456.
Barr et al., (1987), "Antigenicity and immunogenicity of domains of the human immunodeficiency virus (HIV) envelope polypeptide expressed in the yeast *Saccharomyces cerevisiae*.", Vaccine, 5(2): 90-101.
Bhattacharya et al., (2004), "Human Immunodeficiency Virus Type 1 Envelope Glycoproteins That Lack Cytoplasmic Domain Cysteines: Impact on Association with Membrane Lipid Rafts and Incorporation onto Budding Virus Particles.", Journal of Virology, 78(10): 5500-5506.

(Continued)

*Primary Examiner* — Jeffrey S. Parkin
(74) *Attorney, Agent, or Firm* — Emory Patent Group

(57) ABSTRACT

Embodiments of the present disclosure encompasses virus-like particles, methods of making virus-like particles, including expression vectors, wherein the virus-like particles may comprise enhanced levels of capsid-bound a chimeric HN-Env polypeptide compared to VLPs derived from unmodified HIV-env polypeptides. Embodiments of the virus-like particle may have Env-specific epitopes exposed on the outer surface thereof. In one embodiment, the Env-specific epitopes exposed on the outer surface of the virus-like particle may specifically bind with an anti-HIV-Env specific antibody. Embodiments of the disclosure further includes methods of generating an antibody specific to an epitope of an HIV-Env polypeptide, comprising delivering to an animal or a human an effective amount of a suspension of virus-like particles comprising a chimeric HIV-Eny polypeptide, thereby inducing the formation of an antibody specific to an epitope of an HIV-1 eny polypeptide.

13 Claims, 13 Drawing Sheets

(56) References Cited

OTHER PUBLICATIONS

Chakrabarti et al., (1986), "Expression of the HTLV-III envelope gene by a recombinant vaccinia virus.", Nature, 320(6062): 535-537.
Chakrabarti et al., (2002), "Modifications of the Human Immunodeficiency Virus Envelope Glycoprotein Enhance Immunogenicity for Genetic Immunization.", Journal of Virology, 76(11): 5357-5368.
Chertova et al., (2002), "Envelope Glycoprotein Incorporation, Not Shedding of Surface Envelope Glycoprotein (gp120/SU), Is the Primary Determinant of SU Content of Purified Human Immunodeficiency Virus Type 1 and Simian Immunodeficiency Virus.", Journal of Virology, 76(11): 5315-5325.
Chow et al., (2003), "Transformation of Rodent Fibroblasts by the Jaagsiekte Sheep Retrovirus Envelope Is Receptor Independent and Does Not Require the Surface Domain.", Journal of Virology, 77(11): 6341-6350.
Compans et al., (1970), "Influenza virus proteins: I. Analysis of polypeptides of the virion and identification of spike glycoproteins.", Virology, 42(4): 880-889.
Demirov et al., (2004), "Retrovirus budding.", Virus Research, 106(2): 87-102.
Deml et al., (1997), "Increased Incorporation of Chimeric Human Immunodeficiency Virus Type 1 gp120 Proteins into Pr55gagVirus-like Particles by an Epstein-Barr Virus gp220/350—Derived Transmembrane Domain.", Virology, 235(1): 10-25.
Desrosiers, R., (1999), "Strategies used by human immunodeficiency virus that allow persistent viral replication.", Nat Med, 5(7): 723-725.
Freed, E., (2002), "Viral Late Domains.", Journal of Virology, 76(10): 4679-4687.
Gribskov et al., (1986), "Sigma factors from *E. coli, B. subtilis*, phage SP01, and phage T4 are homologous proteins.", Nucleic Acids Research, 14(16): 6745-6763.
Hagensee et al., (1994), "Three-dimensional structure of vaccinia virus-produced human papillomavirus type 1 capsids.", Journal of Virology, 68(7): 4503-4505.
Henriksson et al., (1999), "Incorporation of Wild-Type and C-Terminally Truncated Human Epidermal Growth Factor Receptor into Human Immunodeficiency Virus-Like Particles: Insight into the Processes Governing Glycoprotein Incorporation into Retroviral Particles.", Journal of Virology, 73(11): 9294-9302.
Ho et al., (1989), "Site-directed mutagenesis by overlap extension using the polymerase chain reaction.", Gene, 77(1): 51-59.
Hook et al., (2000), "Genetics of Mouse Mammary Tumor Virus-Induced Mammary Tumors: Linkage of Tumor Induction to the gagGene.", Journal of Virology, 74(19): 8876-8883.
Hu et al., (1987), "Expression of envelope glycoproteins of human immunodeficiency virus by an insect virus vector.", Journal of Virology, 61(11): 3617-3620.
Kang et al. (2005). "Modified HIV envelope proteins with enhanced binding to neutralizing monoclonal antibodies." Virology 331(1): 20-32.
Kieny et al., (1986), "AIDS virus env Protein Expressed from a Recombinant Vaccinia Virus.", Nat Biotech, 4(9): 790-795.
Kochetov et al., (1998), "Eukaryotic mRNAs encoding abundant and scarce proteins are statistically dissimilar in many structural features.", FEBS Letters, 440(3): 351-355.
Lasky et al., (1986), "Neutralization of the AIDS retrovirus by antibodies to a recombinant envelope glycoprotein.", Science, 233(4760): 209-212.
Li et al., (1994), "Control of Expression, Glycosylation, and Secretion of HIV-1 gp120 by Homologous and Heterologous Signal Sequences.", Virology, 204(1): 266-278.
Li et al., (1996), "Effects of inefficient cleavage of the signal sequence of HIV-1 gp 120 on its association with calnexin, folding, and intracellular transport.", Proceedings of the National Academy of Sciences, 93(18): 9606-9611.
Liao et al., (2006), "A group M consensus envelope glycoprotein induces antibodies that neutralize subsets of subtype B and C HIV-1 primary viruses.", Virology, 353(2): 268-282.
Lopez-Verges et al., (2006), "Tail-interacting protein TIP47 is a connector between Gag and Env and is required for Env incorporation into HIV-1 virions." Proceedings of the National Academy of Sciences 103(40): 14947-14952.
McCaughan et al., (1995), "Translational termination efficiency in mammals is influenced by the base following the stop codon.", Proceedings of the National Academy of Sciences, 92(12): 5431-5435.
Perez et al., (2004), "Myristoylation of the Ring Finger Z Protein Is Essential for Arenavirus Budding.", Journal of Virology, 78(20): 11443-11448.
Provitera et al., (2006), "The effect of HIV-1 Gag myristoylation on membrane binding.", Biophysical Chemistry, 119(1): 23-32.
Raghuraman et al., (2004), "Interaction of Melittin with Membrane Cholesterol: A Fluorescence Approach.", Biophysical Journal, 87(4): 2419-2432.
Roberts et al., (1998), "The M1 and M2 Proteins of Influenza A Virus Are Important Determinants in Filamentous Particle Formation.", Virology, 240(1): 127-137.
Rousso et al., (2000), "Palmitoylation of the HIV-1 envelope glycoprotein is critical for viral infectivity." Proceedings of the National Academy of Sciences 97(25): 13523-13525.
Saifuddin et al., (1997), "Human immunodeficiency virus type 1 incorporates both glycosyl phosphatidylinositol-anchored CD55 and CD59 and integral membrane CD46 at levels that protect from complement-mediated destruction.", Journal of General Virology, 78(8): 1907-1911.
Smith et al., (1981), "Comparison of biosequences.", Advances in Applied Mathematics, 2(4): 482-489.
Takefman et al., (1998), "Mechanisms of Resistance of HIV-1 Primary Isolates to Complement-Mediated Lysis." Virology, 246(2): 370-378.
Vzorov et al., (2000), "Effect of the Cytoplasmic Domain of the Simian Immunodeficiency Virus Envelope Protein on Incorporation of Heterologous Envelope Proteins and Sensitivity to Neutralization.", Journal of Virology, 74(18): 8219-8225.
Wang et al., (2007), "Incorporation of High Levels of Chimeric Human Immunodeficiency Virus Envelope Glycoproteins into Virus-Like Particles.", Journal of Virology, 81(20): 10869-10878.
Wyma et al., (2000), "Evidence for a Stable Interaction of gp41 with Pr55Gag in Immature Human Immunodeficiency Virus Type 1 Particles.", Journal of Virology, 74(20): 9381-9387.
Yagi et al., (1977), "Structural components of mouse mammary tumor virus I. Polypeptides of the virion.", Virology, 76 (2): 751-766.
Yamshchikov et al., (1995), "Assembly of SIV Virus-like Particles Containing Envelope Proteins Using a Baculovirus Expression System.", Virology, 214(1): 50-58.
Yang et al., (1996), "Palmitoylation of the Murine Leukemia Virus Envelope Glycoprotein Transmembrane Subunits.", Virology, 221(1): 87-97.
Yao et al., (2000), "Production and characterization of simian—human immunodeficiency virus-like particles.", AIDS Res Hum Retroviruses, 16(3): 227-236.
Ye et al., (2004), "Surface Stability and Immunogenicity of the Human Immunodeficiency Virus Envelope Glycoprotein: Role of the Cytoplasmic Domain.", Journal of Virology, 78(24): 13409-13419.
York et al., (2004), "Role of Hydrophobic Residues in the Central Ectodomain of gp41 in Maintaining the Association between Human Immunodeficiency Virus Type 1 Envelope Glycoprotein Subunits gp120 and gp41.", Journal of Virology, 78(9): 4921-4926.
Yuste et al., (2005), "Virion Envelope Content, Infectivity, and Neutralization Sensitivity of Simian Immunodeficiency Virus.", Journal of Virology, 79(19): 12455-12463.

* cited by examiner

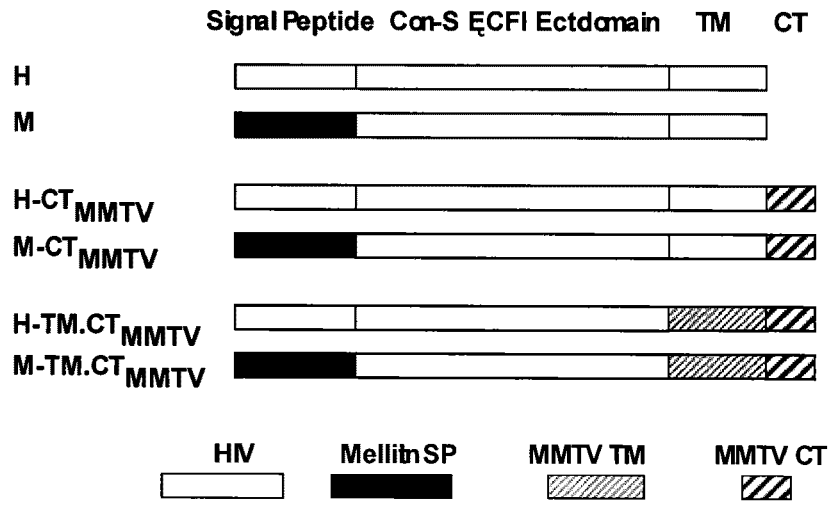
Fig. 1A
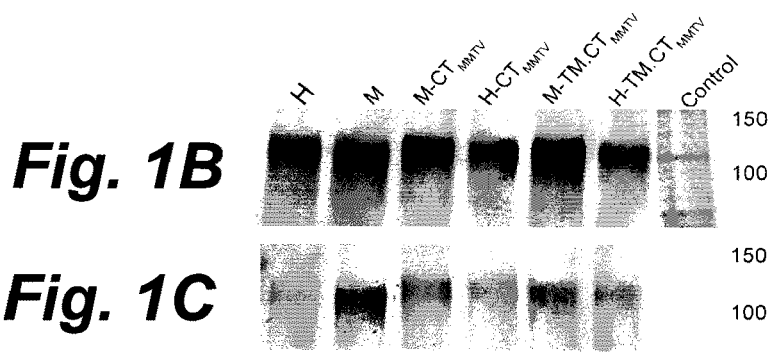
Fig. 1B
Fig. 1C
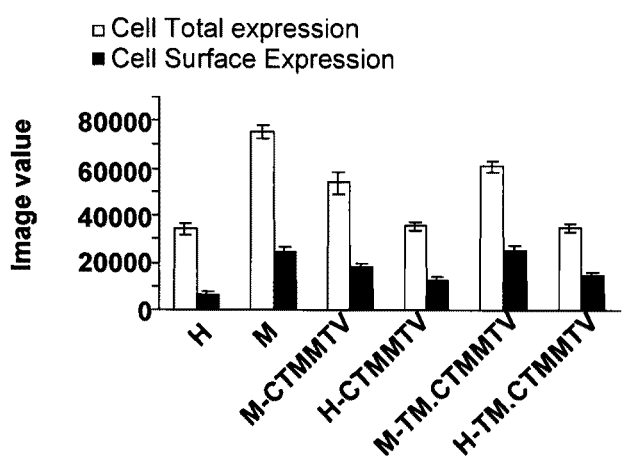
Fig. 1D

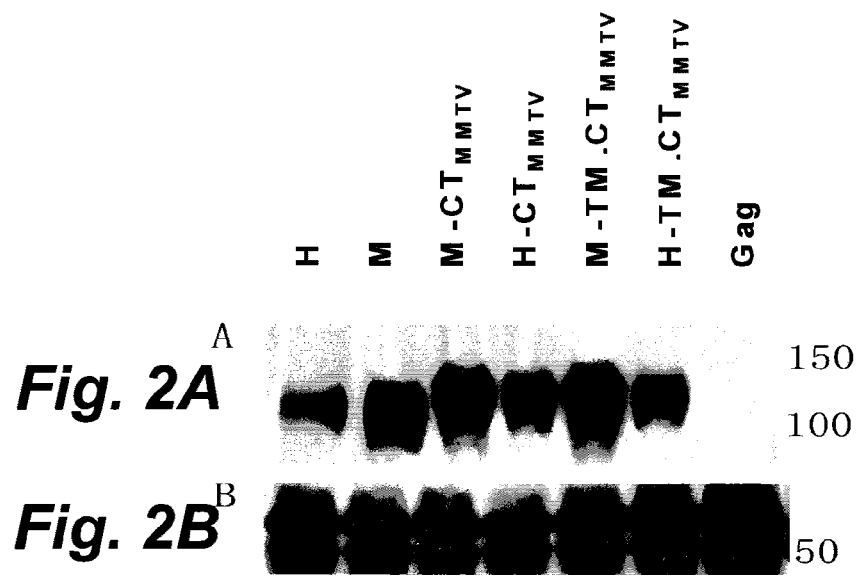
Fig. 2A
Fig. 2B
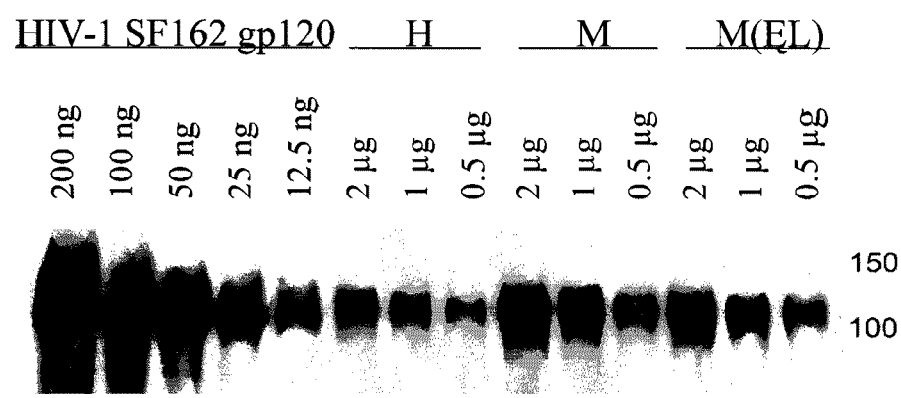
Fig. 2C

|           | HIV-1 SF162 gp120                           | M                     | M-CT$_{MMTV}$         | M-TM.CT$_{MMTV}$      |
|           | 200 ng 100 ng 50 ng 25 ng 12.5 ng | 2 µg 1 µg 0.5 µg | 2 µg 1 µg 0.5 µg | 2 µg 1 µg 0.5 µg |

|              | Signal Peptide | Con-S ECFI Ectodomain | TM | CT |
|--------------|----------------|-----------------------|----|----|
| H            |                |                       |    |    |
| M(EL1)       |                |                       |    |    |
| M-(L2)CT     |                |                       |    |    |
| M-CT$_{MMTVt}$ |              |                       |    |    |
| H-(L2)CT     |                |                       |    |    |
| M-(L3)TM.CT  |                |                       |    |    |
| M-TM.CT$_{MMTVt}$ |           |                       |    |    |
| H-(L3)TM.CT  |                |                       |    |    |

Mellitin SP   ELinker1   MMTV TM   Linker2   MMTV CT   Linker3   MMTV CTt

E Linker1:DPINMT GS;   Linker2: D;   Link3: EF;

*Fig. 3B*

Signal Peptide  Con-S ECFI Ectodomain    TM  CT

H          CT

H-CT$_{LFV}$

H-TM.CT$_{LFV}$

Lassa GP TM    Lassa GP CT

Fig. 5A

Cell lysates  ConB Gag VLPs   LFV Z VLPs

H-CT$_{LFV}$ / H-TM.CT$_{LFV}$ / H-CT$_{LFV}$ / H-TM.CT$_{LFV}$ / M-TM.CT / ConB Gag / H-CT$_{LFV}$ / H-TM.CT$_{LFV}$ / M-TM.CT / LFV Z 250
150
100 — Env
75
50
25
15
10

Fig. 5B

Cell lysates  ConB Gag VLPs   LFV Z VLPs

H-CT$_{LFV}$ / H-TM.CT$_{LFV}$ / H-CT$_{LFV}$ / H-TM.CT$_{LFV}$ / M-TM.CT / ConB Gag / H-CT$_{LFV}$ / H-TM.CT$_{LFV}$ / M-TM.CT / LFV Z conB Gag

LFV Z

SEQ ID NO.: 34
ATGAAATTCTTAGTCAACGTTGCCCTTGTTTTTATGGTCGTGTACATTTCTTACATCTATGCGG
ACCCGATCAACATGACCGGATCCGCCGAGAACCTGTGGGTGACCGTGTACTACGGCGTGCCCGT
GTGGAAGGAGGCCAACACCACCCTGTTCTGCGCCTCCGACGCCAAGGCCTACGACACCGAGGTG
CACAACGTGTGGGCCACCCACGCCTGCGTGCCCACCGACCCCAACCCCCAGGAGATCGTGCTGG
AGAACGTGACCGAGAACTTCAACATGTGGAAGAACAACATGGTGGAGCAGATGCACGAGGACAT
CATCTCCCTGTGGGACCAGTCCCTGAAGCCCTGCGTGAAGCTGACCCCCCTGTGCGTGACCCTG
AACTGCACCAACGTGAACGTGACCAACACCACCAACAACACCGAGGAGAAGGGCGAGATCAAGA
ACTGCTCCTTCAACATCACCACCGAGATCCGCGACAAGAAGCAGAAGGTGTACGCCCTGTTCTA
CCGCCTGGACGTGGTGCCCATCGACGACAACAACAACAACTCCTCCAACTACCGCCTGATCAAC
TGCAACACCTCCGCCATCACCCAGGCCTGCCCCAAGGTGTCCTTCGAGCCCATCCCCATCCACT
ACTGCGCCCCCGCCGGCTTCGCCATCCTGAAGTGCAACGACAAGAAGTTCAACGGCACCGGCCC
CTGCAAGAACGTGTCCACCGTGCAGTGCACCCACGGCATCAAGCCCGTGGTGTCCACCCAGCTG
CTGCTGAACGGCTCCCTGGCCGAGGAGGAGATCATCATCCGCTCCGAGAACATCACCAACAACG
CCAAGACCATCATCGTGCAGCTGAACGAGTCCGTGGAGATCAACTGCACCCGCCCCAACAACAA
CACCCGCAAGTCCATCCGCATCGGCCCCGGCCAGGCCTTCTACGCCACCGGCGACATCATCGGC
GACATCCGCCAGGCCCACTGCAACATCTCCGGCACCAAGTGGAACAAGACCCTGCAGCAGGTGG
CCAAGAAGCTGCGCGAGCACTTCAACAACAAGACCATCATCTTCAAGCCCTCCTCCGGCGGCGA
CCTGGAGATCACCACCCACTCCTTCAACTGCCGCGGCGAGTTCTTCTACTGCAACACCTCCGGC
CTGTTCAACTCCACCTGGATCGGCAACGGCACCAAGAACAACAACAACACCAACGACACCATCA
CCCTGCCCTGCCGCATCAAGCAGATCATCAACATGTGGCAGGGCGTGGGCCAGGCCATGTACGC
CCCCCCCATCGAGGGCAAGATCACCTGCAAGTCCAACATCACCGGCCTGCTGCTGACCCGCGAC
GGCGGCAACAACAACACCAACGAGACCGAGATCTTCCGCCCCGGCGGCGGCGACATGCGCGACA
ACTGGCGCTCCGAGCTGTACAAGTACAAGGTGGTGAAGATCGAGCCCCTGGGCGTGGCCCCCAC
CAAGGCCAAGCTTACCGTGCAGGCCCGCCAGCTGCTGTCCGGCATCGTGCAGCAGCAGTCCAAC
CTGCTGCGCGCCATCGAGGCCCAGCAGCACCTGCTGCAGCTGACCGTGTGGGGCATCAAGCAGC
TGCAGGCCCGCGTGCTGGCCGTGGAGCGCTACCTGAAGGACCAGCAGCTGCTCGAGATCTGGGA
CAACATGACCTGGATGGAGTGGGAGCGCGAGATCAACAACTACACCGACATCATCTACTCCCTG
ATCGAGGAGTCCCAGAACCAGCAGGAGAAGAACGAGCAGGAGCTGCTGGCCCTGGACAAGTGGG
CCTCCCTGTGGAACTGGTTCGACATCACCAACTGGCTGTGGTACATCAAG<u>TTAAATCCATTAGA
TTGGACACAATATTTCATTTTTATAGGTGTTGGAGCCCTGCTTTTAGTCATAGTGCTTATGATC
TTCCCCATCGTGTTCCAGTGCCTGGCCAAGAGCCTGGACCAGGTGCAGAGCGACCTGAACGTGC
TGCTGCTGAAGAAGAAGAAGGGTGGCAACGCCGCCCCGCCGCCGAGATGGTGGAGCTGCCGAG
AGTGTCCTACACCTAATAG</u>

*Fig. 9*

SEQ ID NO: 35
*MKFLVNVALVFMVVYISYIYADPINMTGS*AENLWVTVYYGVPVWKEANTTLFCASDAKAYDT
EVHNVWATHACVPTDPNPQEIVLENVTENFNMWKNNMVEQMHEDIISLWDQSLKPCVKLTPL
CVTLNCTNVNVTNTTNNTEEKGEIKNCSFNITTEIRDKKQKVYALFYRLDVVPIDDNNNNSS
NYRLINCNTSAITQACPKVSFEPIPIHYCAPAGFAILKCNDKKFNGTGPCKNVSTVQCTHGI
KPVVSTQLLLNGSLAEEEIIRSENITNNAKTIIVQLNESVEINCTRPNNNTRKSIRIGPGQ
AFYATGDIIGDIRQAHCNISGTKWNKTLQQVAKKLREHFNNKTIIFKPSSGGDLEITTHSFN
CRGEFFYCNTSGLFNSTWIGNGTKNNNNTNDTITLPCRIKQIINMWQGVGQAMYAPPIEGKI
TCKSNITGLLLTRDGGNNNTNETEIFRPGGGDMRDNWRSELYKYKVVKIEPLGVAPTKAKLT
VQARQLLSGIVQQQSNLLRAIEAQQHLLQLTVWGIKQLQARVLAVERYLKDQQLLEIWDNMT
WMEWEREINNYTDIIYSLIEESQNQQEKNEQELLALDKWASLWNWFDITNWLWYIK<u>LNPLDW</u>
<u>TQYFIFIGVGALLLVIVLMIFPIVFQCLAKSLDQVQSDLNVLLLKKKKGCN</u>AAPAAEMVELP
RVSYT

Fig. 10

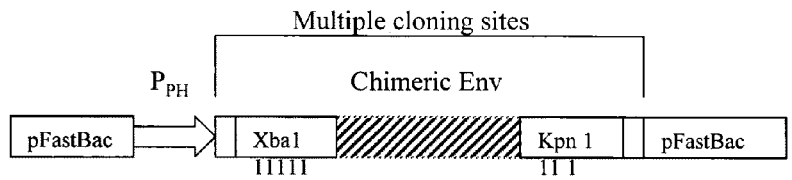

Fig. 11

SEQUENCE LISTING

```
<160> NUMBER OF SEQ ID NOS: 35

<210> SEQ ID NO 1
<211> LENGTH: 22
<212> TYPE: PRT
<213> ORGANISM: Artificial Sequence
<220> FEATURE:
<223> OTHER INFORMATION: Transmembrane region

<400> SEQUENCE: 1

Ile Phe Ile Met Ile Val Gly Gly Leu Ile Gly Leu Arg Ile Val Phe
1               5                   10                  15

Ala Val Leu Ser Ile Val
            20

<210> SEQ ID NO 2
<211> LENGTH: 31
<212> TYPE: PRT
<213> ORGANISM: Artificial Sequence
<220> FEATURE:
<223> OTHER INFORMATION: Transmembrane region

<400> SEQUENCE: 2

Leu Asn Pro Leu Asp Trp Thr Gln Tyr Phe Ile Phe Ile Gly Val Gly
1               5                   10                  15

Ala Leu Leu Leu Val Ile Val Leu Met Ile Phe Pro Ile Val Phe
            20                  25                  30

<210> SEQ ID NO 3
<211> LENGTH: 23
<212> TYPE: PRT
<213> ORGANISM: Artificial Sequence
<220> FEATURE:
<223> OTHER INFORMATION: Transmembrane region

<400> SEQUENCE: 3

Phe Met Phe Gly His Val Val Asn Phe Val Ile Ile Leu Ile Val Ile
1               5                   10                  15

Leu Phe Leu Tyr Cys Met Ile
            20

<210> SEQ ID NO 4
<211> LENGTH: 26
<212> TYPE: PRT
<213> ORGANISM: Artificial Sequence
<220> FEATURE:
<223> OTHER INFORMATION: Transmembrane region

<400> SEQUENCE: 4

Leu Gly Leu Val Asp Leu Phe Val Phe Ser Thr Ser Phe Tyr Leu Ile
1               5                   10                  15

Ser Ile Phe Leu His Leu Ile Lys Ile Pro
            20                  25
```

<210> SEQ ID NO 5
<211> LENGTH: 27
<212> TYPE: PRT
<213> ORGANISM: Artificial Sequence
<220> FEATURE:
<223> OTHER INFORMATION: Transmembrane region

<400> SEQUENCE: 5

Asp Trp Ile Leu Trp Ile Ser Phe Ala Ile Ser Cys Phe Leu Cys
1               5                   10                  15

Val Ala Leu Leu Gly Phe Ile Met Trp Ala Cys
            20                  25

<210> SEQ ID NO 6
<211> LENGTH: 155
<212> TYPE: PRT
<213> ORGANISM: Artificial Sequence
<220> FEATURE:
<223> OTHER INFORMATION: Cytoplasmic tail region

<400> SEQUENCE: 6

Asn Arg Val Arg Gln Gly Tyr Ser Pro Leu Ser Phe Gln Thr Leu Ile
1               5                   10                  15

Pro Asn Pro Arg Gly Pro Asp Arg Pro Glu Gly Ile Glu Glu Glu Gly
            20                  25                  30

Gly Glu Gln Asp Arg Asp Arg Ser Ile Arg Leu Val Asn Gly Phe Leu
        35                  40                  45

Ala Leu Ala Trp Asp Asp Leu Arg Ser Leu Cys Leu Phe Ser Tyr His
    50                  55                  60

Arg Leu Arg Asp Phe Ile Leu Ile Ala Ala Arg Thr Val Glu Leu Leu
65                  70                  75                  80

Gly Arg Lys Gly Leu Arg Arg Gly Trp Glu Ala Leu Lys Tyr Leu Trp
                85                  90                  95

Asn Leu Leu Gln Tyr Trp Gly Gln Glu Leu Lys Asn Ser Ala Ile Ser
            100                 105                 110

Leu Leu Asp Thr Thr Ala Ile Ala Val Ala Glu Gly Thr Asp Arg Val
        115                 120                 125

Ile Glu Val Val Gln Arg Ala Cys Arg Ala Ile Leu Asn Ile Pro Arg
    130                 135                 140

Arg Ile Arg Gln Gly Leu Glu Arg Ala Leu Leu
145                 150                 155

<210> SEQ ID NO 7
<211> LENGTH: 42
<212> TYPE: PRT
<213> ORGANISM: Artificial Sequence
<220> FEATURE:
<223> OTHER INFORMATION: Cytoplasmic tail region

<400> SEQUENCE: 7

Gln Cys Leu Ala Lys Ser Leu Asp Gln Val Gln Ser Asp Leu Asn Val
1               5                   10                  15

Leu Leu Leu Lys Lys Lys Gly Gly Asn Ala Ala Pro Ala Ala Glu
            20                  25                  30

Met Val Glu Leu Pro Arg Val Ser Tyr Thr
            35                  40

<210> SEQ ID NO 8
<211> LENGTH: 36
<212> TYPE: PRT
<213> ORGANISM: Artificial Sequence

```
<220> FEATURE:
<223> OTHER INFORMATION: Cytoplasmic tail region

<400> SEQUENCE: 8

Gln Cys Leu Ala Lys Ser Leu Asp Gln Val Gln Ser Asp Leu Asn Val
1               5                   10                  15

Leu Leu Leu Lys Lys Lys Gly Gly Asn Ala Ala Pro Ala Ala Glu
            20                  25                  30

Met Val Glu Leu
        35

<210> SEQ ID NO 9
<211> LENGTH: 7
<212> TYPE: PRT
<213> ORGANISM: Artificial Sequence
<220> FEATURE:
<223> OTHER INFORMATION: Cytoplasmic tail region

<400> SEQUENCE: 9

Arg Asn Arg Asn Arg Gln Tyr
1               5

<210> SEQ ID NO 10
<211> LENGTH: 38
<212> TYPE: PRT
<213> ORGANISM: Artificial Sequence
<220> FEATURE:
<223> OTHER INFORMATION: Cytoplasmic tail region

<400> SEQUENCE: 10

Thr His Arg His Ile Val Gly Gly Pro Cys Pro Lys Pro His Arg Leu
1               5                   10                  15

Asn His Lys Gly Ile Cys Ser Cys Gly Leu Tyr Lys Arg Pro Gly Val
            20                  25                  30

Ser Val Arg Trp Lys Arg
        35

<210> SEQ ID NO 11
<211> LENGTH: 11
<212> TYPE: PRT
<213> ORGANISM: Artificial Sequence
<220> FEATURE:
<223> OTHER INFORMATION: Cytoplasmic tail region

<400> SEQUENCE: 11

Gln Lys Gly Asn Ile Arg Cys Asn Ile Cys Ile
1               5                   10

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gcaggatccg ccgagaacct gtg                                      23

<210> SEQ ID NO 13
<211> LENGTH: 24
<212> TYPE: DNA
<213> ORGANISM: Artificial Sequence
<220> FEATURE:
<223> OTHER INFORMATION: Primer
```

-continued

<400> SEQUENCE: 13
gctgtcgacg atggacagca cggc    24

<210> SEQ ID NO 14
<211> LENGTH: 59
<212> TYPE: DNA
<213> ORGANISM: Artificial Sequence
<220> FEATURE:
<223> OTHER INFORMATION: Primer

<400> SEQUENCE: 14
ggttctagaa tgaaattctt agtcaacgtt gcccttgttt ttatggtcgt gtacatttc    59

<210> SEQ ID NO 15
<211> LENGTH: 59
<212> TYPE: DNA
<213> ORGANISM: Artificial Sequence
<220> FEATURE:
<223> OTHER INFORMATION: Primer

<400> SEQUENCE: 15
gtgggatccg gtcatgttga tcgggtccgc atagatgtaa gaaatgtaca cgaccataa    59

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
gtgctgtcca tcgtctaagt cgacctcgag ggg    33

<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
gaggtcgact tagacgatgg acagcacggc g    31

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ggtacatcaa gttaaatcca ttag    24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ctaatggatt taacttgatg tacc    24

<210> SEQ ID NO 20
<211> LENGTH: 22

```
<212> TYPE: DNA
<213> ORGANISM: Artificial Sequence
<220> FEATURE:
<223> OTHER INFORMATION: Primer

<400> SEQUENCE: 20
ctgggcccct attaggtgta gg                                        22

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gtgctgtcca tcgtcaagag cctggac                                   27

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
gtccaggctc ttgacgatgg acagcac                                   27

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
ggggatccac acaagcaaga tggtaa                                    26

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
gccgtctcgc ggccgagaac ctgtgggtga cc                             32

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
gccgtctcgc cgcaaaggca gaatgcg                                   27

<210> SEQ ID NO 26
<211> LENGTH: 38
<212> TYPE: DNA
<213> ORGANISM: Artificial Sequence
<220> FEATURE:
<223> OTHER INFORMATION: Primer

<400> SEQUENCE: 26
```
ggaattctta cacgatggac agcacggcga acacgatg                          38

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
gccgtctcaa cttgatgtac cacagccagt t                                31

<210> SEQ ID NO 28
<211> LENGTH: 32
<212> TYPE: DNA
<213> ORGANISM: Artificial Sequence
<220> FEATURE:
<223> OTHER INFORMATION: Primer

<400> SEQUENCE: 28
gccgtctcaa gttcatgttt ggtcatgtag tt                               32

<210> SEQ ID NO 29
<211> LENGTH: 33
<212> TYPE: DNA
<213> ORGANISM: Artificial Sequence
<220> FEATURE:
<223> OTHER INFORMATION: Primer

<400> SEQUENCE: 29
ggaattctta atattgtcta ttacggtttc taa                              33

<210> SEQ ID NO 30
<211> LENGTH: 29
<212> TYPE: PRT
<213> ORGANISM: Artificial Sequence
<220> FEATURE:
<223> OTHER INFORMATION: Signal peptide

<400> SEQUENCE: 30

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala
            20                  25

<210> SEQ ID NO 31
<211> LENGTH: 29
<212> TYPE: PRT
<213> ORGANISM: Artificial Sequence
<220> FEATURE:
<223> OTHER INFORMATION: Signal peptide

<400> SEQUENCE: 31

Met Lys Phe Leu Val Asn Val Ala Leu Val Phe Met Val Val Tyr Ile
1               5                   10                  15

Ser Tyr Ile Tyr Ala Asp Pro Ile Asn Met Thr Gly Ser
            20                  25

<210> SEQ ID NO 32
<211> LENGTH: 20
<212> TYPE: PRT
<213> ORGANISM: Artificial Sequence
<220> FEATURE:
<223> OTHER INFORMATION: Signal peptide

<400> SEQUENCE: 32

Met Val Ser Ala Ile Val Leu Tyr Val Leu Leu Ala Ala Ala Ala His
1               5                   10                  15

Ser Ala Phe Ala
            20

<210> SEQ ID NO 33
<211> LENGTH: 20
<212> TYPE: PRT
<213> ORGANISM: Artificial Sequence
<220> FEATURE:
<223> OTHER INFORMATION: Signal peptide

<400> SEQUENCE: 33

Met Pro Leu Tyr Lys Leu Leu Asn Val Leu Trp Leu Val Ala Val Ser
1               5                   10                  15

Asn Ala Ile Pro
            20

<210> SEQ ID NO 34
<211> LENGTH: 2067
<212> TYPE: DNA
<213> ORGANISM: Artificial Sequence
<220> FEATURE:
<223> OTHER INFORMATION: Chimeric sequence

<400> SEQUENCE: 34

| | |
|---|---:|
| atgaaattct tagtcaacgt tgcccttgtt tttatggtcg tgtacatttc ttacatctat | 60 |
| gcggacccga tcaacatgac cggatccgcc gagaacctgt gggtgaccgt gtactacggc | 120 |
| gtgcccgtgt ggaaggaggc caacaccacc ctgttctgcg cctccgacgc caaggcctac | 180 |
| gacaccgagg tgcacaacgt gtgggccacc cacgcctgcg tgcccaccga ccccaacccc | 240 |
| caggagatcg tgctggagaa cgtgaccgag aacttcaaca tgtggaagaa caacatggtg | 300 |
| gagcagatgc acgaggacat catctcccctg tgggaccagt ccctgaagcc ctgcgtgaag | 360 |
| ctgacccccc tgtgcgtgac cctgaactgc accaacgtga cgtgaccaa ccaccaac | 420 |
| aacaccgagg agaagggcga gatcaagaac tgctccttca acatcaccac cgagatccgc | 480 |
| gacaagaagc agaaggtgta cgccctgttc taccgcctgg acgtggtgcc catcgacgac | 540 |
| aacaacaaca ctcctccaa ctaccgcctg atcaactgca cacctccgc catcacccag | 600 |
| gcctgcccca aggtgtcctt cgagcccatc cccatccact actgcgcccc cgccggcttc | 660 |
| gccatcctga gtgcaacga caagaagttc aacggcaccg cccctgcaa gaacgtgtcc | 720 |
| accgtgcagt gcacccacgg catcaagccc gtggtgtcca cccagctgct gctgaacggc | 780 |
| tccctggccg aggaggagat catcatccgc tccgagaaca tcaccaacaa cgccaagacc | 840 |
| atcatcgtgc agctgaacga gtccgtggag atcaactgca cccgcccaa caacaacacc | 900 |
| cgcaagtcca tccgcatcgg ccccggccag gccttctacg ccaccggcga catcatcggc | 960 |
| gacatccgcc aggcccactg caacatctcc ggcaccaagt ggaacaagac cctgcagcag | 1020 |
| gtggccaaga agctgcgcga gcacttcaac aacaagacca tcatcttcaa gccctcctcc | 1080 |
| ggcggcgacc tggagatcac cacccactcc ttcaactgcc gcggcgagtt cttctactgc | 1140 |
| aacacctccg gcctgttcaa ctccacctgg atcggcaacg caccaagaa caacaacaac | 1200 |
| accaacgaca ccatcaccct gccctgccgc atcaagcaga tcatcaacat gtggcagggc | 1260 |
| gtgggccagg ccatgtacgc ccccccatc gagggcaaga tcacctgcaa gtccaacatc | 1320 |
| accggcctgc tgctgacccg cgacggcggc aacaacaaca ccaacgagac cgagatcttc | 1380 |

-continued

```
cgccccggcg gcggcgacat gcgcgacaac tggcgctccg agctgtacaa gtacaaggtg    1440
gtgaagatcg agcccctggg cgtggccccc accaaggcca agcttaccgt gcaggcccgc    1500
cagctgctgt ccggcatcgt gcagcagcag tccaacctgc tgcgcgccat cgaggcccag    1560
cagcacctgc tgcagctgac cgtgtggggc atcaagcagc tgcaggcccg cgtgctggcc    1620
gtggagcgct acctgaagga ccagcagctg ctcgagatct gggacaacat gacctggatg    1680
gagtgggagc gcgagatcaa caactacacc gacatcatct actccctgat cgaggagtcc    1740
cagaaccagc aggagaagaa cgagcaggag ctgctggccc tggacaagtg ggcctccctg    1800
tggaactggt tcgacatcac caactggctg tggtacatca agttaaatcc attagattgg    1860
acacaatatt tcatttttat aggtgttgga gccctgcttt tagtcatagt gcttatgatc    1920
ttccccatcg tgttccagtg cctggccaag agcctggacc aggtgcagag cgacctgaac    1980
gtgctgctgc tgaagaagaa gaagggtggc aacgccgccc cgccgccga gatggtggag    2040 ctgccgagag tgtcctacac ctaatag                                        2067
```

<210> SEQ ID NO 35
<211> LENGTH: 687
<212> TYPE: PRT
<213> ORGANISM: Artificial Sequence
<220> FEATURE:
<223> OTHER INFORMATION: Protein translation

<400> SEQUENCE: 35

```
Met Lys Phe Leu Val Asn Val Ala Leu Val Phe Met Val Val Tyr Ile
1               5                   10                  15

Ser Tyr Ile Tyr Ala Asp Pro Ile Asn Met Thr Gly Ser Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
    130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240
```

-continued

```
Thr Val Gln Cys Thr His Gly Ile Lys Pro Val Ser Thr Gln Leu
                    245                 250                 255

Leu Leu Asn Gly Ser Leu Ala Glu Glu Ile Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
    290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
            340                 345                 350

Thr Ile Ile Phe Lys Pro Ser Gly Gly Asp Leu Glu Ile Thr Thr
        355                 360                 365

His Ser Phe Asn Cys Arg Gly Glu Phe Phe Tyr Cys Asn Thr Ser Gly
    370                 375                 380

Leu Phe Asn Ser Thr Trp Ile Gly Asn Gly Thr Lys Asn Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
            420                 425                 430

Lys Ile Thr Cys Lys Ser Asn Ile Thr Gly Leu Leu Leu Thr Arg Asp
        435                 440                 445

Gly Gly Asn Asn Asn Thr Asn Glu Thr Glu Ile Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Leu Thr
                485                 490                 495

Val Gln Ala Arg Gln Leu Leu Ser Gly Ile Val Gln Gln Ser Asn
            500                 505                 510

Leu Leu Arg Ala Ile Glu Ala Gln Gln His Leu Leu Gln Leu Thr Val
        515                 520                 525

Trp Gly Ile Lys Gln Leu Gln Ala Arg Val Leu Ala Val Glu Arg Tyr
    530                 535                 540

Leu Lys Asp Gln Gln Leu Leu Glu Ile Trp Asp Asn Met Thr Trp Met
545                 550                 555                 560

Glu Trp Glu Arg Glu Ile Asn Asn Tyr Thr Asp Ile Ile Tyr Ser Leu
                565                 570                 575

Ile Glu Glu Ser Gln Asn Gln Gln Glu Lys Asn Glu Gln Glu Leu Leu
            580                 585                 590

Ala Leu Asp Lys Trp Ala Ser Leu Trp Asn Trp Phe Asp Ile Thr Asn
        595                 600                 605

Trp Leu Trp Tyr Ile Lys Leu Asn Pro Leu Asp Trp Thr Gln Tyr Phe
    610                 615                 620

Ile Phe Ile Gly Val Gly Ala Leu Leu Leu Val Ile Val Leu Met Ile
625                 630                 635                 640

Phe Pro Ile Val Phe Gln Cys Leu Ala Lys Ser Leu Asp Gln Val Gln
                645                 650                 655

Ser Asp Leu Asn Val Leu Leu Leu Lys Lys Lys Lys Gly Gly Asn Ala
```

-continued

```
            660                 665                 670

Ala Pro Ala Ala Glu Met Val Glu Leu Pro Arg Val Ser Tyr Thr
        675                 680                 685
```

VIRUS-LIKE PARTICLES COMPRISING CHIMERIC HUMAN IMMUNODEFICIENCY VIRUS (HIV)/MOUSE MAMMARY TUMOR VIRUS (MMTV) ENVELOPES

CROSS REFERENCE TO RELATED APPLICATION

This application claims priority to the PCT application entitled "Enhancement of Glycoprotein Incorporation Into Virus-Like Particles," having serial number PCT/US2008/62516, filed on May 2, 2008. This application also claims priority to and benefit of U.S. Provisional Patent Application No. 60/927,208, filed on May 2, 2007, which is incorporated by reference in its entirety.

STATEMENT ON FUNDING PROVIDED BY THE U.S. GOVERNMENT

This invention was made with government support under NIH Grants Nos. AI028147 awarded by the U.S. National Institutes of Health of the United States government. The government has certain rights in the invention

BACKGROUND

In the life cycle of human immunodeficiency virus (HIV)-1, assembly of the virion particle is an important step which is regulated by both viral and cellular factors (Demirov, 2004; Lopez-Verges, 2006). The HIV Gag protein is sufficient for assembly, budding and release from the host cell of virus-like particles (VLPs). Each particle is enveloped by a lipid bilayer derived from the host cell; and the envelope glycoprotein (Env) is incorporated into the particle during the process of assembly (Deml, 1997; Yao, 2000). The Gag has a "late" (L) domain that promotes particle release by interacting with components of the cellular endosomal sorting pathway (Freed, 2002). Gag is also post-translationally modified with an N-terminal myristate group, which is thought to target Gag to lipid rafts thus aiding in assembly (Provitera, 2006).

It has been reported that the transmembrane (TM) and cytoplasmic tail (CT) domains of gp41 exert a key role in incorporation of the HIV-1 envelope glycoprotein (Env) during HIV assembly. The TM and CT domains of HIV-1 and SIV Env have important effects on the orientation, surface expression, surface stability and Env incorporation into particles (Zingler, 1993; Vzorov, 2000; Ye, 2004). Previous studies suggest that specific regions in Env are involved in the interaction with Gag in assembly (Lopez-Verges, 2006; Demirov, 2004); however, the detailed mechanisms that determine the incorporation of Env into VLPs remain to be determined. It is also not well understood whether different viral core proteins have preferences for their cognate Env or whether heterologous CT/TM-CT sequences prefer a specific matrix protein for assembly into VLPs.

In early studies, it was observed that HIV-1 Env is expressed and secreted very inefficiently in various expression systems including yeast (Barr, 1987) and mammalian cells (Lasky, 1986; Chakrabarti, 1986; Kieny, 1986). The signal sequence is important in directing Env to the endoplasmic reticulum and eventually to the cell surface. The substitution of the HIV Env signal peptide (SP) with that from honeybee mellitin was shown to promote higher level expression and secretion of HIV-1 gp120 (Li, 1994). HIV-1 Env also has a CT sequence with over 150 amino acids (aa) whereas glycoproteins of other viruses including MMTV, Lassa fever virus (LFV), BV gp64, and influenza virus HA have much shorter CT sequences between 7 to 43 aa in length. Interestingly, these viruses with shorter CT sequences incorporate their glycoprotein into virions at much higher levels than those in HIV-1 (Compans, 1978).

SUMMARY

Embodiments of the present disclosure encompasses virus-like particles, methods of making virus-like particles, including expression vectors, wherein the virus-like particles may comprise enhanced levels of capsid-bound a chimeric HIV-Env polypeptide compared to VLPs derived from unmodified HIV-env polypeptides. In an embodiment, the virus-like particle may have Env-specific epitopes exposed on the outer surface thereof. In an embodiment, the Env-specific epitopes exposed on the outer surface of the virus-like particle may specifically bind with an anti-HIV-Env specific antibody. Embodiments of the present disclosure further include methods of generating an antibody specific to an epitope of an HIV-Eny polypeptide, comprising delivering to an animal or a human an effective amount of a suspension of virus-like particles comprising a chimeric HIV-Env polypeptide, thereby inducing the formation of an antibody specific to an epitope of an HIV-1 eny polypeptide.

In an embodiment, the HIV envelope (Env) protein is incorporated into HIV virions or virus-like particles (VLPs) at very low levels compared with glycoproteins of most other enveloped viruses. In an embodiment, a series of chimeric gene constructs were made in which the coding sequences for the signal peptide (SP), transmembrane (TM) and cytoplasmic (CT) domains of HIV-1 Env were replaced with those of other viral or cellular proteins individually or in combination. In an embodiment, all constructs tested were derived from HIV-1 Con-S ΔCFI gp145, which itself is incorporated into VLPs much more efficiently than full-length ConS Env. In an embodiment, substitution of the SP from the honeybee protein mellitin resulted in 3-fold higher levels of expression of chimeric HIV-1 Env on insect cell surfaces, enhanced CD4-binding, and a significant increase of Env incorporation into VLPs. In an embodiment, CT or TM-CT substitutions with sequences derived from the mouse mammary tumor virus (MMTV) envelope glycoprotein, influenza HA or baculovirus gp64 were found to significantly enhance Env incorporation into VLPs.

One aspect of the present disclosure, therefore, encompasses recombinant nucleic acids encoding a chimeric HIV-Env polypeptide, wherein the recombinant nucleic acid comprises a first domain encoding a heterologous signal peptide, wherein the first domain is operably linked to a second domain encoding an HIV-Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region. In one embodiment of the disclosure, the first domain encodes a signal peptide derived from honeybee mellitin.

In embodiments of the disclosure, the second domain may encode a chimeric HIV-1 Con-S ΔCFI env polypeptide.

In embodiments of the disclosure, the third domain encodes a polypeptide comprising the mouse mammary tumor virus TM and CT amino acid sequences. In one embodiment of this aspect of the disclosure, the chimeric HIV-Env polypeptide may comprise a mellitin signal peptide, the chimeric HIV-1 Con-S ΔCFI env polypeptide, and mouse mammary tumor virus TM and CT amino acid sequences.

In the various embodiments of the recombinant nucleic acid of the disclosure, the recombinant nucleic acid may be operably linked to an expression promoter, and in one embodiment of the disclosure, the recombinant nucleic acid may be operably incorporated into an expression vector, and wherein the expression vector can be selected from the group consisting of a plasmid vector, a viral vector, a baculoviral vector, a bacmid, and an artificial chromosome.

In one embodiment, the vector is a baculoviral vector. In another embodiment, the baculoviral vector is a bacmid vector, and the region encoding the chimeric HIV-Env polypeptide may be codon optimized for expression in an insect cell.

Another aspect of the disclosure are expression vectors comprising: an expression promoter operably linked to a recombinant nucleic acid encoding a chimeric HIV-Env polypeptide, wherein the recombinant nucleic acid comprises a first domain encoding a heterologous signal peptide, wherein the first domain is operably linked to a second domain encoding an HIV-Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region.

Yet another aspect of the present disclosure encompasses virus-like particles comprising about 2% to about 30% of a chimeric HIV-Env polypeptide. In one embodiment of this aspect of the disclosure, the virus-like particle may have Env-specific epitopes exposed on the outer surface thereof. In one embodiment, the Env-specific epitopes exposed on the outer surface of the virus-like particle may specifically bind with an anti-HIV-Env specific antibody.

In an embodiment, the virus-like particles may be produced by cotransfecting a eukaryotic host cell with a first expression vector and a second expression vector, wherein the first expression vector expresses an HIV-1 gag polypeptide, and wherein the second expression vector expresses a chimeric HIV-Env polypeptide, the second expression vector comprising an expression promoter operably linked to a recombinant nucleic acid encoding, wherein the recombinant nucleic acid comprises a first domain encoding a heterologous signal peptide, wherein the first domain is operably linked to a second domain encoding an HIV-Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region; and allowing the cotransfected host cell to form the virus-like particles. In one embodiment of the disclosure, the virus-like particles may be isolated by centrifugation.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-1D illustrates effects of SP substitution on total expression and cell surface expression of chimeric Con-S ΔCFI Env in Sf9 cells infected with rBVs. FIG. 1A, Schematic diagram of modified chimeric HIV-1 Con-S ΔCFI Env: All components of the original HIV-1 gene are shown as empty boxes. The other components of chimeric segments are shown schematically by designations shown below. FIG. 1B illustrates the total cellular expression. FIG. 1C illustrates the cell surface expression. FIG. 1D illustrates the relative amounts in B and C quantified by PhosphorImager analysis. Sf9 cells were infected with rBV at an m.o.i. of 4 PFU/cell. At 48 hr postinfection, the synthesized proteins were metabolically labeled with [$^{35}$S] met/cys, and cell surface proteins were identified by biotin labeling. Samples were resolved by SDS-PAGE, and the gel was dried and used for autoradiography and PhosphorImager analysis. The image values were used for comparison of cell cellular total expression and cell surface expression.

FIG. 2 illustrates effect of SP substitution on the incorporation of Env into VLPs. VLPs were produced by coexpression of ConB Gag and chimeric Env constructs, and concentrated by centrifugation through a 15% sucrose cushion. The protein concentration of resulting VLPs was determined with a Bio-Rad protein assay kit. A and B: Two μg of total VLP protein were used for Western blot analysis; FIG. 2A: goat anti-HIV-1 Env gp120 polyclonal antibody was used as primary binding antibody; FIG. 2B: mouse anti-HIV-1 Gag polyclonal antibody was used for ConB Gag detection. FIG. 2C: Different amounts (μg/well) of HIV-1 SF162 gp120, H, M and M-(ΔL1) VLPs were loaded for western blot analysis as indicated.

FIG. 3 illustrates effects of MMTV TM, TM-CT and flexible connecting regions on Env incorporation into VLPs. FIG. 3A: Different amounts of HIV-1 SF162 gp120, M, M-CT$_{MMTV}$ and M-TM.CT$_{MMTV}$ were loaded for western blot analysis as shown. FIG. 3B: Schematic diagram of modified chimeric HIV-1 Con-S ΔCFI Env. The deleted linker 1(L1) is DPINMTGS. L2 and L3 represent D and EF respectively. For M-CT$_{MMTVt}$ and M-TM.CT$_{MMTVt}$, a six-amino acid fragment, PRVSYT, was truncated at the C-terminal of MMTV CT.

FIG. 4 illustrates comparison of heterologous chimeric HIV-1 Env incorporated into VLPs.

FIG. 5 illustrates western blot analysis of VLPs produced using Lassa GP-derived CT or TM-CT chimeric Env proteins. FIG. 5A: Schematic diagram of chimeric Con-S Env fused with Lassa virus GP-derived CT/TM-CT. The coding sequence for the Lassa virus glycoprotein CT (Lassa GP aa 450 to 491) or TM-CT (Lassa GP aa 427 to 491) was fused to that of the C-terminal of Con-S ΔCFI. FIG. 5B: Western blot of protein expression in cell lysates and VLPs probed using goat anti-HIV-1 gp120 antibody; FIG. 5C: Western blot of VLP matrix proteins (1 μg/well) released in VLPs probed with a mixture of mouse anti-HIV-1 Gag and anti-Lassa Z antibody mixture.

FIG. 6 illustrates comparison of Env incorporation into VLPs with different core proteins. One microgram of VLP samples was loaded for each lane. For western blot, anti-HIV-1 Env, anti-HIV-1 Gag, anti-Lassa protein Z and anti-influenza M1 antibody mixture was used for primary binding in the blot.

FIG. 7 illustrates the analysis of conserved antigenic regions on Env-enriched VLPs. For FIGS. 7A to 7D: surface plasmon resonance assays were performed as described in Materials and Methods. The VLP concentration used for binding was 1.25 mg/ml (Env level 95 μg/ml). SF162 gp120 (150 μg/ml) was used as a positive control. For the detection of the ability of VLPs to bind to sCD4 or T8, sCD4 and T8 were covalently immobilized to a CM5 sensor chip (BIAcore), the VLPs or control was injected over each surface, and the binding was recorded. For determination of induction of 17b MAb binding, VLPs and control were captured on individual flow cells immobilized with sCD4 or T8. After stabilization of each surface, MAb 17b was injected and allowed to flow over each of the immobilized cells.

FIG. 8 illustrates electron microscopy of HIV VLPs.

FIG. 9 illustrates the HIV chimeric Env encoding DNA sequence (SEQ ID NO.: 34). The mellitin signal peptide encoding sequence is in italic; the ConS dCFI ectodomain encoding sequence is in regular case; and the MMTV TM-CT encoding sequence is underlined.

FIG. 10 illustrates HIV chimeric Env amino acid sequence (SEQ ID NO.: 35). The mellitin signal peptide encoding sequence is in italics; ConS dCFI ectodomain encoding sequence is in regular case; and the MMTV TM-CT encoding sequence is underlined.

FIG. 11 illustrates that the chimeric Env encoding DNA sequence was subcloned into transfer vector pFastBac-1 with Xba 1/Kpa 1 under polyhedron promoter ($P_{PH}$) as shown below.

Figure 1E:
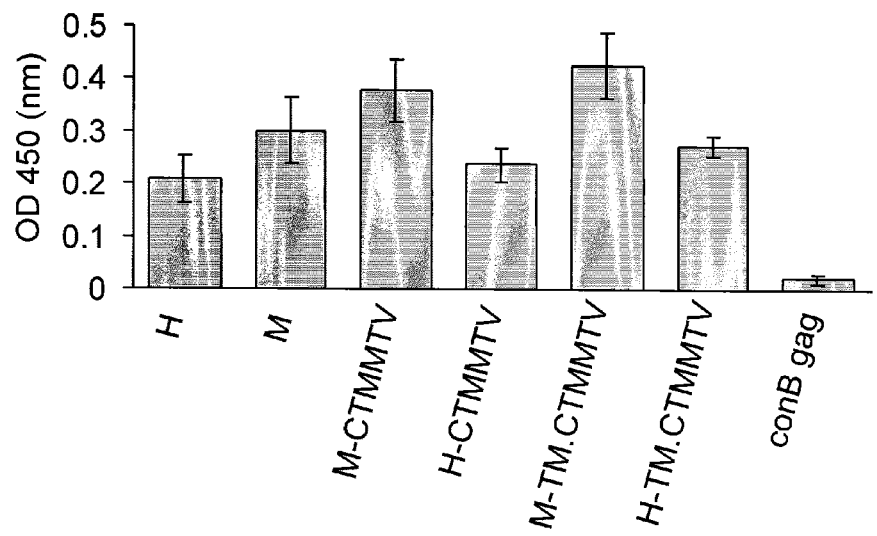
FIG. 1E illustrates the CD-4 binding activity of cell surface expressed Con-S chimeric proteins. Sf9 cells infected with rBV expressing chimeric HIV-1 Con-S constructs, at an MOI of 4 PFU/cell, were fixed, and the CD4 binding levels were determined by using a cell-based ELISA. Relative CD4-binding capacity is expressed as the optical density at 450 nm.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION OF THE DISCLOSURE

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

"DNA" refers to the polymeric form of deoxyribonucleotides (adenine, guanine, thymine, or cytosine) in either single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "modify the level of gene expression" as used herein refers to generating a change, either a decrease or an increase in the amount of a transcriptional or translational product of a gene. The transcriptional product of a gene is herein intended to refer to a messenger RNA (mRNA) transcribed product of a gene and may be either a pre- or post-spliced mRNA. Alternatively, the term "modify the level of gene expression" may refer to a change in the amount of a protein, polypeptide or peptide generated by a cell as a consequence of interaction of an siRNA with the contents of a cell. For example, but not limiting, the amount of a polypeptide derived from a gene may be reduced if the corresponding mRNA species is subject to degradation as a result of association with an siRNA introduced into the cell.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. An "isolated" nucleic acid molecule is one that is separated from other nucleic acid molecules that are present in the natural source of the nucleic acid. A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

The term "transfection" refers to a process by which agents are introduced into a cell. The list of agents that can be transfected is large and includes, but is not limited to, siRNA, sense and/or anti-sense sequences, DNA encoding one or more genes and organized into an expression plasmid, proteins, protein fragments, and more. There are multiple methods for transfecting agents into a cell including, but not limited to, electroporation, calcium phosphate-based transfections, DEAE-dextran-based transfections, lipid-based transfections, molecular conjugate-based transfections (e.g., polylysine-DNA conjugates), microinjection and others.

As used herein, the terms "sub-viral particle" "virus-like particle" or "VLP" refer to a nonreplicating, viral shell, preferably derived entirely or partially from HIV proteins. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. See, e.g., Baker et al., Biophys. J. (1991) 60:1445-1456; Hagensee et al., J. Virol. (1994) 68:4503-4505. For example, VLPs can be isolated by density gradient centrifugation and/or identified by characteristic density banding (e.g., Examples). Alternatively, cryoelectron microscopy can be performed on vitrified aqueous samples of the VLP preparation in question, and images recorded under appropriate exposure conditions.

By "particle-forming polypeptide" derived from a particular viral (e.g., from an HIV) protein is meant a full-length or near full-length viral protein, as well as a fragment thereof, or a viral protein with internal deletions, insertions or substitutions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, vatine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γδ (gamma DELTA T)-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, see e.g., McCaughan et al. (1995) PNAS USA 92:5431-5435; Kochetov et al (1998) FEBS Letts. 440:351-355.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

A "vector" is a genetic unit (or replicon) to which or into which other DNA segments can be incorporated to effect replication, and optionally, expression of the attached segment. Examples include, but are not limited to, plasmids, cosmids, viruses, chromosomes and minichromosomes. Exemplary expression vectors include, but are not limited to, baculovirus vectors, modified vaccinia Ankara (MVA) vectors, plasmid DNA vectors, recombinant poxvirus vectors, bacterial vectors, recombinant baculovirus expression systems (BEVS), recombinant rhabdovirus vectors, recombinant alphavirus vectors, recombinant adenovirus expression systems, recombinant DNA expression vectors, and combinations thereof.

A "coding sequence" is a nucleotide sequence that is transcribed into mRNA and translated into a protein, in vivo or in vitro.

"Regulatory sequences" are nucleotide sequences, which control transcription and/or translation of the coding sequences, which they flank.

"Processing sites" are described in terms of nucleotide or amino acid sequences (in context of a coding sequence or a polypeptide). A processing site in a polypeptide or nascent peptide is where proteolytic cleavage occurs, where glycosylation is incorporated or where lipid groups (such as myristoylation) occurs. Proteolytic processing sites are where proteases act.

"Virosomes" or "virus-like particles (VLPs)" are lipid vesicles having viral envelope proteins expressed on the virosome surface. In addition, adjuvant molecules can be expressed on the virosome. Additional components of virosomes, as known in the art, can be included within or disposed on the virosome. Virosomes do not contain intact viral nucleic acids, and they are non-infectious. Desirably, there is sufficient viral surface envelope glycoprotein and/or adjuvant molecules expressed, at least in part, on the surface of the virosome so that when a virosome preparation is formulated into an immunogenic composition and administered to an animal or human, an immune response (cell-mediated or humoral) is raised.

A "truncated" viral surface envelope glycoprotein is one having less than a full length protein (e.g., a portion of the cytoplasmic domain has been removed), which retains surface antigenic determinants against which an immune response is generated, preferably a protective immune response, and it retains sufficient envelope sequence for proper membrane insertion. The skilled artisan can produce truncated virus envelope proteins using recombinant DNA technology and virus coding sequences, which are readily available to the public.

As used herein "chimeric" viral surface glycoproteins are ones that contain at least a portion of the extracellular domain of a viral surface glycoprotein of one virus and at least a portion of domains and/or signal peptide sequence of a different transmembrane glycoprotein from a different virus or other organism. Such chimeric proteins retain surface antigenic determinants against which an immune response is generated, preferably a protective immune response, and retain sufficient envelope sequence for proper precursor processing and membrane insertion. The skilled artisan can produce chimeric viral surface glycoproteins using recombinant DNA technology and protein coding sequences, techniques known to those of skill in the art and available to the public. Such chimeric viral surface glycoproteins may be useful for increasing the level of incorporation of viral glycoproteins in virosomes for viruses that may naturally have low levels of incorporation.

In an embodiment, a "chimeric" VLP can at least one viral surface envelope glycoprotein incorporated into the VLP, wherein the viral core protein and at least one viral surface envelope glycoprotein are from different viruses. In an embodiment, a chimeric VLP may include additional viral surface envelope glycoproteins that are from the same or different virus as the viral core protein, so long as at least one is different.

In an embodiment, a "phenotypically mixed" VLP can be defined as a VLP having at least two different surface molecules (e.g., surface envelope glycoproteins and/or adjuvant molecules) incorporated into the VLP. In an embodiment, a phenotypically mixed VLP, as used herein, may include additional surface molecules that are from the same or different source as the viral core protein, so long as at least one is different.

In an embodiment, the term "adjuvant molecule" refers to surface proteins capable of eliciting an immune response in a host. In particular embodiments, the adjuvant molecule is a "membrane-anchored form" of the adjuvant molecule which indicates that the adjuvant molecule has been engineered to include a signal peptide (SP) and a membrane anchor sequence to direct the transport and membrane orientation of the protein. Thus, in embodiments, a membrane-anchored form of an adjuvant molecule is a recombinant protein including a portion of a protein fused to a SP and membrane anchor sequence.

In an embodiment, an adjuvant molecule, or at least a portion of an adjuvant molecule, is disposed (e.g., expressed) on the surface of the virosome or VLP. The adjuvant molecule can interact with other molecules or cells.

The adjuvant molecule can include, but is not limited to, an influenza hemagglutinin (HA) molecule (GenBank access number J02090), a parainfluenza hemagglutinin-neuraminidase (HN) molecule (GenBank access number z26523 for human parainfluenza virus type 3 HN sequence information), a Venezuelan equine encephalitis (VEE) adjuvant molecule (GenBank access number nc001449), a fms-like tyrosine kinase ligand (Flt3) adjuvant molecule (GenBank access number NM013520), a C3d adjuvant molecule (GenBank access number nm009778 for mouse C3 sequence and access number nm000064 for human C3 sequence), a mannose receptor adjuvant molecule, a CD40 ligand adjuvant molecule (GenBank access number m83312 for mouse CD40), and combinations thereof. The adjuvant molecule can also include membrane anchored forms of a mammalian toll-like receptor (TLR) ligand molecule, a MIP-1α molecule, a RANTES MIP-1β molecule, a GM-CSF molecule, a Flt3 ligand molecule, a CD40 ligand molecule, an IL-2 molecule, an IL-10 molecule, an IL-12 molecule, an IL-15 molecule, an IL-18 molecule, and an IL-21 molecule, and combinations thereof. Examples of membrane-anchored forms of mammalian TLR ligand molecules include, but are not limited to, ligands listed in Akira, S. and Takeda, K. Toll-Like Receptor Signalling. *Nature Reviews/Immunology*, 4: 499-511 (2004), which is incorporated by reference herein. In particular, exemplary TLR ligand molecules include glycoproteins from *Prevotella intermedia*, Respiratory syncytial virus protein F, fibronectin A domain, fibrinogen, a bacetrial flagellin, a measles virus HA protein, and Pam2Cys lipoprotein/lipopeptide (MALP-2). In some particular embodiments the adjuvant molecule includes a membrane-anchored bacterial flagellin.

In general, the adjuvant molecule sequence and the corresponding polynucleotide sequence can be found in GenBank, and the access numbers can be obtained online at the NCBI. In addition, the sequences identified for the adjuvant molecules above are only illustrative examples of representative adjuvant molecules. Further, variants that are substantially homologous to the above referenced adjuvant molecules and adjuvant molecules having conservative substitutions of the above referenced adjuvant molecules can also be incorporated into virosomes or VLPs of the present disclosure to enhance the immunogenic characteristics of virosomes or VLP.

In another embodiment, polyclonal and/or monoclonal antibodies capable of specifically binding to the virosome are provided. The term "antibody" is used to refer both to a homogenous molecular entity, or a mixture such as a serum product made up of a plurality of different molecular entities. Monoclonal or polyclonal antibodies, which specifically react with the virosomes of the present disclosure, may be made by methods known in the art. (e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987)). Also, recombinant immunoglobulin may be produced by methods known in the art, including but not limited to, the methods described in U.S. Pat. No. 4,816,567, which is hereby incorporated by reference herein.

Antibodies specific for virosomes and viral surface envelope glycoproteins of viruses may be useful, for example, as probes for screening DNA expression libraries or for detecting the presence of the cognate virus in a test sample. Frequently, the polypeptides and antibodies will be labeled by joining, either covalently or noncovalently, a substance that provides a detectable signal. Suitable labels include, but are not limited to, radionuclides, enzymes, substrates, cofactors, inhibitors, fluorescent agents, chemiluminescent agents, magnetic particles and the like. United States Patents describing the use of such labels include, but are not limited to, U.S. Pat. Nos. 3,817,837; 3,850,752; 3,939,350; 3,996,345; 4,277, 437; 4,275,149; and 4,366,241, which are hereby incorporated by reference herein for the corresponding discussion.

Antibodies specific for virosomes and retroviral surface envelope glycoproteins may be useful in treating animals, including humans, suffering from cognate viral disease. Such antibodies can be obtained by the methods described above and subsequently screening the viral surface envelope glycoproteins-specific antibodies for their ability to inhibit virus uptake by target cells.

Compositions and immunogenic preparations of the present disclosure, including vaccine compositions, comprising the virosomes of the present disclosure and capable of inducing protective immunity in a suitably treated host and a suitable carrier therefore are provided. "Immunogenic compositions" are those which result in specific antibody production or in cellular immunity when injected into a host. Such immunogenic compositions or vaccines are useful, for example, in immunizing hosts against infection and/or damage caused by viruses, including, but not limited to, HIV, human T-cell leukemia virus (HTLV) type I, SIV, FIV, SARS, RVFV, Filovirus, Flavivirus, arenavirus, bunyavirus, paramyxovirus, influenza virus, cytomegalovirus, herpesvirus, alphavirus, and flavivirus.

The vaccine preparations of the present disclosure can include an immunogenic amount of one or more virosomes, fragment(s), or subunit(s) thereof. Such vaccines can include one or more viral surface envelope glycoproteins and portions thereof, and adjuvant molecule and portions thereof on the surfaces of the virosomes, or in combination with another protein or other immunogen, such as one or more additional virus components naturally associated with viral particles or an epitopic peptide derived therefrom.

By "immunogenic amount" is meant an amount capable of eliciting the production of antibodies directed against the virus, in the host to which the vaccine has been administered. It is preferred for HIV and HTLV, among others, that the route of administration and the immunogenic composition is designed to optimize the immune response on mucosal surfaces, for example, using nasal administration (via an aerosol) of the immunogenic composition.

Immunogenic carriers can be used to enhance the immunogenicity of the virosomes from any of the viruses discussed herein. Such carriers include, but are not limited to, proteins and polysaccharides, microspheres formulated using (e.g., a biodegradable polymer such as DL-lactide-coglycolide, liposomes, and bacterial cells and membranes). Protein carriers may be joined to the proteinases, or peptides derived therefrom, to form fusion proteins by recombinant or synthetic techniques or by chemical coupling. Useful carriers and ways of coupling such carriers to polypeptide antigens are known in the art.

The immunogenic compositions and/or vaccines of the present disclosure may be formulated by any of the methods known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active immunogenic ingredients are often mixed with excipients or carriers, which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable, aerosol or nasal formulations is usually in the range of about 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or other agents, which enhance the effectiveness of the vaccine. Examples of agents which may be effective include, but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of the auxiliary substances may be determined by measuring the amount of antibodies (especially IgG, IgM or IgA) directed against the immunogen resulting from administration of the immunogen in vaccines which comprise the adjuvant in question. Additional formulations and modes of administration may also be used.

The immunogenic compositions and/or vaccines of the present disclosure can be administered in a manner compatible with the dosage formulation, and in such amount and manner as will be prophylactically and/or therapeutically effective, according to what is known to the art. The quantity to be administered, which is generally in the range of about 1 to 1,000 micrograms of viral surface envelope glycoprotein per dose and/or adjuvant molecule per dose, more generally in the range of about 5 to 500 micrograms of glycoprotein per dose and/or adjuvant molecule per dose, depends on the nature of the antigen and/or adjuvant molecule, subject to be treated, the capacity of the hosts immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response (e.g., at 1 to 4 months for a second dose, and if needed, a subsequent dose(s) after several months). Humans (or other animals) immunized with the virosomes of the present disclosure are protected from infection by the cognate virus.

It should also be noted that the vaccine or immunogenic composition can be used to boost the immunization of a host having been previously treated with a different vaccine such as, but not limited to, DNA vaccine and a recombinant virus vaccine.

Except as noted hereafter, standard techniques for peptide synthesis, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) Experiments in Molecular Genetics, Cold Spring Harbor Laboratory, Cold Spring Harbor, N.Y., Old Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) *Genetic Engineering: Principles and Methods*, Vols. 1-4, Plenum Press, N.Y.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. Hosts that are "predisposed to" condition(s) can be defined as hosts that do not exhibit overt symptoms of one or more of these conditions but that are genetically, physiologically, or otherwise at risk of developing one or more of these conditions.

The term "treat", "treating", and "treatment" are an approach for obtaining beneficial or desired clinical results. For purposes of embodiments of this disclosure, beneficial or desired clinical results include, but are not limited to, alleviation of symptoms, diminishment of extent of disease, stabilization (e.g., not worsening) of disease or conditions, preventing spread of disease or conditions, delaying or slowing of disease progression or condition, amelioration or palliation of the disease state or condition, and remission (partial or total) whether detectable or undetectable. In addition, "treat", "treating", and "treatment" can also mean prolonging survival as compared to expected survival if not receiving treatment.

In an embodiment, the term "condition" and "conditions" denote a state of health that can be related to infection by a virus. Infections can include be included as conditions that can be treated by an embodiment of the present disclosure.

Discussion

Embodiments of the present disclosure encompasses virus-like particles, methods of making virus-like particles, including expression vectors, wherein the virus-like particles may comprise enhanced levels of capsid-bound a chimeric HIV-Env polypeptide compared to VLPs derived from unmodified HIV-env polypeptides. In an embodiment, the virus-like particle may have Env-specific epitopes exposed on the outer surface thereof. In an embodiment, the Env-specific epitopes exposed on the outer surface of the virus-like particle may specifically bind with an anti-HIV-Env specific antibody. Embodiments of the present disclosure further include methods of generating an antibody specific to an epitope of an HIV-Eny polypeptide, comprising delivering to an animal or a human an effective amount of a suspension of virus-like particles comprising a chimeric HIV-Env polypeptide, thereby inducing the formation of an antibody specific to an epitope of an HIV-1 eny polypeptide.

Embodiments of the disclosure discuss and describe the effects of various SP and TM-CT substitutions on the level of incorporation of HIV-1 Env into recombinant baculovirus (rBV) derived Gag VLPs. In addition, embodiments of the present disclosure compared the efficacy of different viral core proteins in incorporating chimeric HIV-1 Env with cognate or heterologous TM-CT domain.

To investigate determinants of Env assembly into virus particles, we compared a series of chimeric HIV-1 Env proteins with heterologous SP, TM, or CT sequences individually or in combination for their effects on Env incorporation into VLPs. We observed that substitution of the natural HIV SP with the mellitin SP resulted in a modest increase of both intracellular and cell surface expression of chimeric HIV-1 Con-S ΔCFI Env and resulted in about a two-fold enhancement of its incorporation into VLPs, implicating a role of the SP sequence in the transport and assembly of membrane-anchored HIV Env proteins. In contrast, we did not observe significant effects of substitutions with either chitinase SP or BV gp64 SP compared to the parental HIV-1 Env construct.

The long CT domain of HIV-1 Env contains two cysteine residues (C764 and C837) which are targets for palmitoylation (Yang, 1996) and have been implicated in Env targeting to detergent-resistant lipid rafts, Env incorporation into the virus, and viral infectivity (Rousso, 2000). It was suggested that the full-length CT may play a regulatory role in limiting the amount of HIV-1 Env to 7 to 14 trimeric molecules per virion, since truncation of the CT increased Env incorporation by up to 10-fold (Chertova, 2002). This is consistent with our observation that significant enhancement in Env incorporation into VLPs was achieved with ConS ΔCFI Env, or with chimeric constructs with a short heterologous CT or a complete deletion of the CT. However, CT-deleted Env was not found to be stably anchored into VLPs, as a significant amount of CT-deleted HIV-1 Env was lost after a series of purification steps. In contrast, Env fused to MMTV, HA, or BV gp64 TM-CT sequences showed more stable incorporation into VLPs. Therefore, although the CT sequence is not required for incorporation into virions, it may be used for stably anchoring the HIV-1 Env into the lipid bilayer of enveloped virus particles or VLPs.

Substitutions of HIV-1 Env TM-CT sequences with those from glycoproteins of other enveloped viruses (e.g., MMTV, LFV, BV, influenza) increase the level of Env incorporation into corresponding virus particles. MMTV and influenza virus can incorporate glycoproteins at levels up to 58% and 29% of total virion proteins, respectively (Compans, 1970; Yagi, 1977). The glycoproteins of these viruses have much shorter CT sequences than that of HIV-1 (Table 1).

TABLE 1

TM-CT sequences of Con-S Env, MMTV Env, BV gp64, LFZ glycoprotein, and influenza virus HA

| Glycoprotein | Sequence | SEQ ID NO.: |
|---|---|---|
| Transmembrane | | |
| Con-S Env | IFIMTVGGLIGLRIVFAVLSIV | 1 |
| MMTV Env | LNPLDWTQYFIFIGVGALLLVIVLMIFPIVF | 2 |
| BV gp64 | FMFGHVVNFVIILIVILFLYCMI | 3 |
| LFVGP | LGLVDLFVFSTSFYLISIFLHLIKIP | 4 |
| Influenza virus HA | DWILWISFAISCFLLCVALLGFIMWAC | 5 |

TABLE 1-continued

TM-CT sequences of Con-S Env, MMTV Env, BV gp64,
LFZ glycoprotein, and influenza virus HA

| Glycoprotein | Sequence | SEQ ID NO.: |
|---|---|---|
| Cytoplasmic Tail | | |
| Con-S Env | NRVRQGYSPLSFQTLIPNPRGPDRPEGIEEEGGE QDRDRSIRLVNGFLALAWDDLRSLCLFSYHRLRD FILIAARTVELLGRKGLRRGWEALKYLWNLLQYW GQELKNSAISLLDTTAIAVAEGTDRVIEVVQRAC RAILNIPRRIRQGLERALL | 6 |
| MMTV Env | QCLAKSLDQVQSDLNVLLLKKKKGGNAAPAAEMV ELPRVSYT | 7 |
| MMTV Env minus PRVSYT | QCLAKSLDQVQSDLNVLLLKKKKGGNAAPAAEMV EL | 8 |
| BV gp64 | RNRNRQY | 9 |
| LFVGP | THRHIVGGPCPKPHRLNHKGICSCGLYKRPGVSV RWKR | 10 |
| Influenza virus HA | QKGNIRCNICI | 11 |

HIV VLPs have been found to contain approximately 1.5% of Env when produced in BV expression system (Sailaja et al., 2007). In the present disclosure, the highest level of Env incorporation into VLPs was observed with a chimeric construct with the MMTV TM-CT (M-TM.CT$_{MMTV}$) in which the molar ratio of Gag:Env was estimated to be 4:1, which is 14-fold higher than that observed with the full-length Con-S gp160 with a 55.7:1 ratio (Table 2), and 15-fold higher than that of SIV or HIV-1 virions with 60:1 ratio (Chertova, 2002).

TABLE 2

Env and Gag content in different chimeric Env VLPs

| VLPs | M-TM.CT$_{MMTV}$ | C-TM.CT$_{HA}$ | B-TM.CT$_{BV}$ | ConS gp160 | Gag |
|---|---|---|---|---|---|
| Env content* | 8.7 | 3.6 | 7.9 | 0.81 | — |
| Gag content* | 13.1 | 14.7 | 13.7 | 15.5 | 17.4 |
| Gag/Env Molar Ratio** | 4.0 | 10.8 | 4.6 | 55.7 | — |

*Env and Gag contents represent μg/100 μg VLPs;
**The molecular weights used for the ratio calculation: M-TM.CT$_{MMTV}$, C-TM.CT$_{HA}$ and B-TM.CT$_{BV}$, 145 kDa; ConS gp160, 160 kDa; Gag, 55 kDa.

The chimeric HIV-1 Env constructs with TM-CT from BV gp64 was also found to be incorporated into VLPs at similarly high levels. These results indicate that the TM/CT sequences of viral glycoproteins play a role in their assembly, and suggest that the low level of incorporation of HIV Env into virions or VLPs is due, in large part, to a restriction imposed by the extended cytoplasmic domain.

Interestingly, a chimeric HIV-1 Env with a TM-CT sequence derived from the LFV GP protein was not effectively incorporated into VLPs despite its expression in insect cells. The arenavirus family including LFV has an unusually long and stable signal peptide (SSP) with a length of 58 aa which is known to be associated with the mature form of arenavirus gp (York, 2004). The chimeric Env containing the influenza HA TM/CT sequences showed enhanced incorporation into VLPs at lower levels than found with the respective MMTV of gp64 sequences. Thus, specific structural features may play a role in optimizing Env incorporation into particles.

Previous studies suggested that interactions of CT domains of viral Env and their corresponding matrix proteins were important for lipid raft association and Env incorporation (Bhattacharya, 2004; Wyma, 2000). Thus, we expected that cognate interactions between viral matrix proteins and the CT domain of Env would play a role in Env incorporation into VLPs. Surprisingly, the chimeric M-TM.CT$_{MMTV}$ construct showed similar levels of Env incorporated into VLPs produced using four different viral matrix proteins (MMTV Gag, HIV Gag, LFV Z, influenza M1), indicating that there is little or no preferential interaction between cognate matrix protein and CT sequences during assembly. HIV Gag, MMTV Gag, and LFV Z are known to have N-terminal myristoylation (Provitera, 2006; Perez, 2004; Chow, 2003). Influenza M1 was reported to interact with the CT and TM domains of HA, probably in the lipid raft domain (Roberts, 1998). Thus, it is possible that all of these viral matrix proteins preferentially associate with a lipid raft domain where the chimeric Env with TM-CT is localized. However, differential effects on the incorporation of the CT-negative Env were observed among the matrix proteins tested. LFV Z and influenza virus M1 matrix proteins were found to be much less effective in incorporating the CT-deleted Env into VLPs compared to MMTV Gag or HIV Gag. Previous studies have demonstrated that retrovirus particles can also incorporate various host cell membrane proteins (Vzorov, 2000), indicating that there are less strict requirements for assembly of envelope proteins into these particles.

VLPs have been demonstrated to be potent HIV-1 candidate vaccines. Recent reports have proven that HIV Env-containing VLPs elicit both arms of immunity and induce specific immune responses at local and distal mucosal surfaces (Buonaguro et al., 2002, Deml et al., 1997; Yao et al., 2003, Doan et al., 2005). Therefore, chimeric VLPs with an enhanced Env incorporation present a promising immunogen for the development of an effective, safe AIDS vaccine. In addition, VLP vaccines with alternative heterologous core proteins will allow a serological discrimination of vaccines and HIV-infected persons in future vaccination studies.

One aspect of the present disclosure encompasses recombinant nucleic acids encoding a chimeric HIV-Env polypeptide, wherein the recombinant nucleic acid comprises a first domain encoding a heterologous signal peptide, wherein the first domain is operably linked to a second domain encoding an HIV-Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region.

In one embodiment of the disclosure, the first domain encodes a signal peptide derived from honeybee mellitin.

In an embodiment of the disclosure, the signal peptide derived from honeybee mellitin has the amino acid sequence according to SEQ ID NO.: 31.

In embodiments of the disclosure, the second domain may encode a chimeric HIV-1 Con-S ΔCFI env polypeptide.

In embodiments of the disclosure, the amino acid sequence of the heterologous transmembrane region is selected from one or more of the sequences according to SEQ ID NOs.: 1-5.

In the embodiments of this aspect of the disclosure, the amino acid sequence of the heterologous cytoplasmic tail region is selected from one or more the sequences according to SEQ ID NOs.: 6-11.

In one embodiment of the disclosure, the third domain encodes a polypeptide comprising one or more of the amino acid sequences SEQ ID NOs.: 2 and 7.

In an embodiment of this aspect of the disclosure, the chimeric HIV-Env polypeptide may comprise the amino acid sequences SEQ ID NO.: 31, the chimeric HIV-1 Con-S ΔCFI env polypeptide, and one or more of SEQ ID NOs.: 2 and 7.

In the various embodiments of the recombinant nucleic acid of the disclosure, the recombinant nucleic acid may be operably linked to an expression promoter.

In one embodiment of the disclosure, the recombinant nucleic acid is operably incorporated into an expression vector, and wherein the expression vector can be selected from the group consisting of a plasmid vector, a viral vector, a baculoviral vector, a bacmid, and an artificial chromosome.

In one embodiment, the vector is a baculoviral vector. In another embodiment, the baculoviral vector is a bacmid vector.

In these embodiments, the region encoding the chimeric HIV-Env polypeptide may be codon optimized for expression in an insect cell.

Another aspect of the disclosure includes expression vectors comprising: an expression promoter operably linked to a recombinant nucleic acid encoding a chimeric HIV-Env polypeptide, wherein the recombinant nucleic acid comprises a first domain encoding a heterologous signal peptide, wherein the first domain is operably linked to a second domain encoding an HIV Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region.

In one embodiment of this aspect of the disclosure, the first domain encodes a signal peptide derived from honeybee mellitin.

In one embodiment, the signal peptide derived from honeybee mellitin has the amino acid sequence according to SEQ ID NO.: 31.

In other embodiments of the disclosure, the second domain may encode a chimeric HIV-1 Con-S ΔCFI env polypeptide.

In various embodiments of this aspect of the disclosure, the amino acid sequence of the heterologous transmembrane region may be selected from one or more of the sequences according to SEQ ID NOs.: 1-5.

In other embodiments of the disclosure, the amino acid sequence of the heterologous cytoplasmic tail region may be selected from one or more of the sequences according to SEQ ID NOs.: 6-11.

In other embodiments of the disclosure, the third domain may encode a polypeptide comprising one or more of the amino acid sequences SEQ ID NOs.: 2 and 7.

In one embodiment of the disclosure, the chimeric HIV-Env polypeptide may comprise the amino acid sequences SEQ ID NO.: 31, the chimeric HIV-1 Con-S ΔCFI env polypeptide, and one or more of SEQ ID NOs.: 2 and 7.

In one embodiment, the expression vector is in a transfected eukaryotic host cell.

In yet another embodiment of the disclosure, the nucleic acid sequence encoding the chimeric HIV-Env polypeptide may be codon optimized for expression in an insect cell.

Yet another aspect of the present disclosure encompasses virus-like particles comprising about 2% to about 30% of an HIV-Env polypeptide.

In one embodiment of this aspect of the disclosure, the virus-like particle may have Env-specific epitopes exposed on the outer surface thereof. In one embodiment, the Env-specific epitopes exposed on the outer surface of the virus-like particle may specifically bind with an anti-HIV-Env specific antibody.

In another embodiment of this aspect of the disclosure, the virus-like particles may be produced by cotransfecting a eukaryotic host cell with a first expression vector and a second expression vector, wherein the first expression vector expresses an HIV-1 gag polypeptide, and wherein the second expression vector expresses a chimeric HIV-Env polypeptide, the second expression vector comprising an expression promoter operably linked to a recombinant nucleic acid encoding, wherein the recombinant nucleic acid comprises a first domain encoding a heterologous signal peptide, wherein the first domain is operably linked to a second domain encoding an HIV-Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region; and allowing the cotransfected host cell to form the virus-like particles. In one embodiment of the disclosure, the virus-like particles may be isolated by centrifugation.

In one embodiment of the disclosure, the first domain of the second expression vector may encode a signal peptide derived from honeybee mellitin. In one embodiment, the signal peptide derived from honeybee mellitin has the amino acid sequence according to SEQ ID NO.: 31.

In another embodiment of this aspect of the disclosure, the second domain of the second expression vector may encode the chimeric HIV-1 Con-S ΔCFI env polypeptide.

In yet another embodiment, the amino acid sequence of the heterologous transmembrane region may be selected from one or more of the sequences according to SEQ ID NOs.: 1-5.

In still another embodiment of the disclosure, the amino acid sequence of the heterologous cytoplasmic tail region is selected from one or more of the sequences according to SEQ ID NOs.: 6-11.

In one embodiment, the third domain may encode a polypeptide comprising one or more of the amino acid sequences SEQ ID NOs.: 2 and 7.

In another embodiment of the disclosure, the chimeric HIV-Env polypeptide may comprise the amino acid sequences SEQ ID NO.: 31, the chimeric HIV-1 Con-S ΔCFI env polypeptide, and one or more of SEQ ID NOs.: 2 and 7.

In the various embodiments of this aspect of the disclosure, the nucleic acid sequence encoding the chimeric HIV-Env polypeptide is codon optimized for expression in an insect cell.

Still another aspect of the disclosure are methods of generating an antibody specific to an epitope of an HIV-Eny polypeptide, comprising delivering to an animal or a human an effective amount of a suspension of virus-like particles comprising a chimeric HIV-Env polypeptide, thereby inducing the formation of an antibody specific to an epitope of an HIV-1 eny polypeptide.

In one embodiment of this aspect of the disclosure, the suspension of virus-like particles further comprises a pharmaceutical carrier and an adjuvant.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Construction of Chimeric Con-S Env Genes

The Con-S ΔCFI gp145 gene is a derivative of the consensus HIV-1 group M ConS env gene which lacks the gp120-gp41 cleavage (C) site, the fusion (F) peptide, an immunodominant (I) region in gp41, as well as a CT domain [Liao, 2006] (H in FIG. 1). All PCR primers used for generating chimeric constructs are listed in Table 3.

TABLE 3

Sequences of the primers sued for cloning.

| Primer | Sequence | SEQ ID NO. |
|---|---|---|
| $F_{BamH1}$: | GCAGGATCCGCCGAGAACCTGTG | SEQ ID NO.: 12 |
| $R_{SalI}$: | GCTGTCGAC GATGGACAGCACGGC | SEQ ID NO.: 13 |
| $F_{melittin}$: | GGTTCTAGAATGAAATTCTTAGTCAACG TTGCCCTTGTTTTTATGGTCGTGTACAT TTC | SEQ ID NO.: 14 |
| $R_{melittin}$ | GTGGGATCCGGTCATGTTGATCGGGTCCG CATAGATGTAAGAAATGTACACGACCATAA | SEQ ID NO.: 15 |
| $F_{val}$, | GTGCTGTCCATCGTCTAAGTCGACCTCGAGGGG | SEQ ID NO.: 16 |
| $R_{val}$, | GAGGTCGACTTAGACGATGGACAGCACGGCG | SEQ ID NO.: 17 |
| $F_{M-TM.CTMMTV}$ | GGTACATCAAGTTAAATCCATTAG | SEQ ID NO.: 18 |
| $R_{M-TM.CTMMTV}$ | CTAATGGATTTAACTTGATGTACC | SEQ ID NO.: 19 |
| $R_{ApaI}$ | CTGGGCCCCTATTAGGTGTAGG | SEQ ID NO.: 20 |
| $F_{M-CTMMTV}$ | GTGCTGTCCATCGTCAAGAGCCTGGAC | SEQ ID NO.: 21 |
| $R_{M-CTMMTV}$ | GTCCAGGCTCTTGACGATGGACAGCAC | SEQ ID NO.: 22 |
| pSP64U1 | GGGGATCCACACAAGCAAGATGGTAA | SEQ ID NO.: 23 |
| Sgp160BsmB1-F | GCCGTCTCGCGGCCGAGAACCTGTGGGTGACC | SEQ ID NO.: 24 |
| pSP64BsmB1-R | GCCGTCTCGCCGCAAAGGCAGAATGCG | SEQ ID NO.: 25 |
| pConS145R | GGAATTCTTACACGATGGACAGCACGGCG AACACGATG | SEQ ID NO.: 26 |

TABLE 3-continued

Sequences of the primers sued for cloning.

| Primer | Sequence | SEQ ID NO. |
|---|---|---|
| S145BsmBI | GCCGTCTCAACTTGATGTACCACAGCCAGTT | SEQ ID NO.: 27 |
| SP64BsmBI | GCCGTCTCAAGTTCATGTTTGGTCATGTAGTT | SEQ ID NO.: 28 |
| SP64CT-R | GGAATTCTTAATATTGTCTATTACGGTTTCTAA | SEQ ID NO.: 29 |

Based on this H construct, the signal peptide sequence and stop codon-deleted intermediate construct (sp-H) was generated by PCR using primers of $F_{BamH\ I}$ and $R_{Sal\ I}$. The PCR product was cloned into vector pBluescript II KS (pBlue) in the polylinker site with BamH I and Sal I, and the resulting sp-H construct was used to generate other chimeric HIV-1 Env mutants. The mellitin SP (sequence in Table 4) with a 6 aa linker DPINMT was described previously ([Raghuraman, 2004; Li, 1994], and the corresponding DNA was synthesized through over-lapping primer extension by PCR with primers $F_{melittin}$ and $R_{melittin}$.

TABLE 4

Signal Peptide Sequences of HIV-1, Mellitin, BV gp64 and Chitinase.

| SP | Sequence | Positively charged residues | |
|---|---|---|---|
| HIV-1 | MRVKGIRNCQHLWRWGTLILGMLMICSA | 5 | SEQ ID NO.: 30 |
| Mellitin | MKFLVNVALVFMVVYISYIYADPINMTGS | 1 | SEQ ID NO.: 31 |
| BV gp64 | MVSAIVLYVLLAAAHSAFA | 1 | SEQ ID NO.: 32 |
| Chitinase | MPLKLLNVLWLVAVSNAIP | 1 | SEQ ID NO.: 33 |

This mellitin SP coding sequence was cloned into the sp-H construct at Xba I and BamH I sites (pBlue-pre-M). Then, a valine and a stop codon were introduced into pBlue-pre-M using two primers $F_{val}$ and $R_{val}$ resulting in the construct pBlue-M (M in FIG. 1A).

To fuse the MMTV TM-CT to the chimeric HIV-1 Con-S ΔCFI env gene, the 73 aa-long MMTV Env TM-CT-encoding gene (616 to 688aa, sequence in Table 1) [Hook, 2000] (protein ID: AAF31475) was codon-optimized, synthesized by primer overlapping extension PCR, and cloned into pBlue with EcoR I and Apa I (pBlue-MMTV-TM/CT). The HIV-1 Env ectodomain with the mellitin SP from pBlue-pre-M was amplified using $F_{melittin}$ and $R_{M-TM.CTMMTV}$ primers, and MMTV-TM/CT amplified using $F_{M-TM.CTMMTV}$ and $R_{Apa\ I}$ primers. These two DNA fragments were fused by overlapping PCR extension [Ho, 1989], and the resulting construct was designated M-CT.$CT_{MMTV}$ (FIG. 1A). Similarly, the M-CT$_{MMTV}$ gene was constructed by overlapping PCR using pBlue-M and pBlue-MMTV-TM/CT as templates (M-CT$_{MMTV}$ in FIG. 1A). Primers used for this over-lapping PCR were $F_{melittin}$, $F_{M-CTMMTV}$, $R_{M-CTMMTV}$ and $R_{Apa\ I}$. To construct H-CT$_{MMTV}$ and H-TM.CT$_{MMTV}$ containing the natural HIV-1 Env SP, the Xba I and Hind III enzymatic fragments (SP plus partial Ectodomain) of M-CT$_{MMTV}$ and M-TM.CT$_{MMTV}$ were replaced with the same enzymatic fragment from H (pBlue Con-S ΔCFI gp145), resulting in constructs designated H-CT$_{MMTV}$ and H-TM.CT$_{MMTV}$ (FIG. 1A).

A baculovirus gp64 glycoprotein derived chimeric Con-S ΔCFI Env gene was constructed by replacing the HIV-1 derived SP, TM and CT domains with the corresponding regions of the baculovirus gp64 glycoprotein. The SP64 signal peptide (20 amino acids) was amplified from pBACsurf-1 (EMD Bioscience, San Diego, Calif.) using pSP64U1 and pSP64BsmB1-R. A ConSΔCFIgp145 gene fragment that lacked the cognate signal peptide was amplified using primers Sgp160BsmB1-F and pConS145R. These fragments were concatenated using a BsmB1 restriction enzyme site and cloned into pFastBac-1. SP64-ConSΔCFIgp140 was then amplified using primers pSP64U1 and S145BsmBI, and the SP64 TM-CT domain was amplified from pBACsurf-1 using primers SP64BsmBI and SP64CT-R. These two fragments were ligated at an internal BsmB1 site which generated pFastBac-1-SP64-ConSΔCFIgp140-SP64TM-CT. This chimeric env gene was cloned into pFastBac-Dual which was modified by inserting the SP64 promoter downstream of the polh promoter, resulting in the construct designated B-TM. CT$_{BV}$ To construct an influenza HA derived chimeric Con-S ΔCFI Env gene, the HIV-1 signal peptide was replaced with chitinase SP (sequence in Table 4) derived from Autographa californica Nuclear Polyhedrosis Virus (AcNPV) chitinase gene. The TM and CT domains of Con-S were replaced with the corresponding C-terminal region of influenza HA that contained putative transmembrane and carboxy terminal sequences derived from influenza A/Fujian/411/02 (H3N2) hemagglutinin (sequence in Table 1). The chimeric gene was codon-optimized for high-level expression in Sf9 cells and synthesized by primer overlapping extension PCR. The resulting PCR fragment was introduced into pFastBac1 transfer vector (Invitrogen) using RsrII and NotI sites within the pFastBac1 polylinker. The identity of all constructs was confirmed by sequence analysis.

Example 2

Generation of Recombinant Baculovirus (rBVs)

The confirmed chimeric Con-S genes were subcloned into the Xba I and Kpn I sites of pFastBac™I transfer vector under the polyhedrin promoter. rBVs were generated using the Bac-to-Bac Expression System (Invitrogen) following the manufacturer's instruction. Briefly, pFastBac plasmids containing chimeric ConS ΔCFI HIV-1 env genes were transformed into DH10Bac competent cells (Invitrogen Life Sciences), white colonies screened in the LB media containing antibiotics kanamycin (50 µg/ml), gentamycin (7 µg/ml), and tetracycline (10 µg/ml) and X-gal and IPTG. After 3 cycles of white colony screening, recombinant Bacmid baculovirus DNAs (rAcNPV) were isolated and transfected into Sf9 insect cells using a Cellfectin reagent (Invitrogen Life Sciences). Transfected culture supernatants were harvested and plaques purified. The expression of chimeric ConS HIV-1 Env proteins from rBV infected cells was confirmed by Western blot.

For the generation of an HIV-1 Gag expressing rBV, we synthesized a codon usage optimized version of the 2002 consensus subtype B gag gene (GenBank accession number EF428978). For a similar rBV construct expressing the Lassa protein Z, its gene sequence encoding 99 amino acids including 11 amino acids of an influenza hemagglutinin (HA) epitope was synthesized optimized for both mammalian and insect cell expression (DNA2.0 Inc, Menlo Park, Calif.) {Eichler, 2004}. Each of these synthetic genes was subcloned into transfer vector pFastBac vector under the polyhedrin promoter. To generate rBVs of the influenza M1 and MMTV Gag, their encoding sequences {Deen, 1986; Galarza, 2005} were subcloned into transfer vector pFastBac under the polyhedrin promoter. These resulting pFastBac plasmids were used to generate rBVs following the same procedure as used for the generation of the chimeric Con-S Env rBVs as described above. The protein expression from rBV-infected insect cells was confirmed by Western blot.

Example 3

Cell Surface Expression Assay

Sf9 cells were seeded to 6-well plates at $1 \times 10^6$ cells/well. Recombinant BV infection, expression and isotopic labeling were performed as described [Yamshchikov, 1995] with modification. In brief, Sf9 cells were infected with rBV at a M.O.I. of 4 PFU/cell for 1 hr at RT. The inoculum was removed and replaced with fresh Sf-900 II SFM medium (Gibco) plus 1% fetal bovine serum (FBS). At 48 hr postinfection, virus-infected cells were placed in methionine and cysteine-free SF-900 II SFM medium for 45 min. Cells were then labeled with 250 µCi/ml of [$^{35}$S]methionine/cysteine (Amersham) for 4 hr. Biotinylation of cell surface proteins was carried out as described [Yang, 1996]. The final samples were loaded onto SDS-PAGE. Gels were dried and then used for X-ray film exposure and phosphorImager analysis.

Example 4

CD4-Binding Assay

Sf9 cells were seeded into 96-well plates at $2 \times 10^4$ cells per well and infected with rBVs as described above. Soluble CD4-binding to cell surfaces was performed as described [Kang, 2005] with modification In brief, at 48 hr post infection, cells were washed 3 times with chilled PBS on ice-bath and fixed with 0.05% gluteraldehyde in PBS at 4° C. for 1 hr. After washing with PBS, cells were incubated with soluble human CD4 at a concentration of 5 µg/ml in PBS at RT for 1 hr. After washing 5 times with PBS, the amount of bound CD4 was determined using rabbit anti-human CD4 serum (1:10, 000) followed by horse-radish peroxidase (HRP) conjugated goat anti-rabbit IgG polyclonal antibody (1:2000). Staining development was performed with a one step substrate TMB (Zemed labs) and $OD_{450}$ was read with an ELISA reader (MTX Lab System).

Example 5

VLP Preparation

Sf9 cells were seeded in a 75 cm T-flask with $1 \times 10^7$ cells. After complete settling (about 1 hr at RT), cells were co-infected with chimeric Env and Con-B Gag rBVs at M.O.I. of 8 and 2, respectively. After 72 hr, media were clarified at 8000 rpm for 25 min. VLPs were pelleted at 12000 g for 1 hr through a 15% sucrose cushion, resuspended with PBS and stored at 4° C. for further analysis.

Example 6

Determination of Env and Gag Contents in VLPs

A sandwich ELISA was employed for Env quantitation. Goat anti-HIV-1 gp120 polyclonal antibody was used as a coating antibody and a mixture of monoclonal antibodies, b12 and F425, were used as detection antibodies. HIV-1 SF162 gp120 (NIH AIDS Research and Reference Reagent Program, catalog number: 7363) was used as calibration standard. For Gag quantitation, a commercial HIV-1 p24 kit (Beckman Coulter) was used following the manufacturer's protocol. An sf2 p55 (NIH AIDS Research and Reference Reagent Program, catalog Number: 5109) was used as a calibration standard.

Example 7

Electron Microscopy

Negative staining. VLP samples (5-10 µl) were applied onto a carbon-coated film. Five minutes later, the remainder was removed with filter paper. Ten µl of 1% sodium phosphotungstate was applied onto the grid and samples were stained for 30 seconds. The staining solution was removed and the grid was dried for 15-30 minutes at RT and observed by electron microscopy.

Example 8

Design of Chimeric Env Proteins

To determine the effects of the signal peptide and TM-CT domains on the incorporation of Env into VLPs, three pairs of genes encoding chimeric Env were initially constructed for comparison (FIG. 1A). In pair I, the Con-S ΔCFI gp145 construct (H) is an HIV-1 group M consensus envelope gene with shortened variable loops, deletions of the cleavage site, the fusion domain and an immunodominant region in gp41 (ΔCFI), and a truncation of the cytoplasmic domain [Liao, 2006]. The ΔCFI form of the protein was reported to improve the ability to assemble into trimers and was shown to be an immunogen with enhanced capability to induce neutralizing antibodies in mice [Chakrabarti, 2002]. Compared to the H construct, the M construct employed the mellitin SP to replace the HIV-1 SP of H Env. The comparison of H and M was intended to reveal the effect of the heterologous mellitin SP, previously reported to lead to more efficient gp120 expression and secretion in an insect cell system [Li, 1994]. In pair II, the MMTV CT was added to the C-termini of both H and M constructs, resulting in the chimeric constructs H-CT$_{MMTV}$ and M-CT$_{MMTV}$. This modification was designed to explore the effect of a short heterologous CT on Env incorporation into VLPs and to compare the results with the CT truncated constructs in pair I. In pair III, the MMTV TM-CT was used to substitute for the corresponding regions in pair II, resulting in H-TM.CT$_{MMTV}$ and M-TM.CT$_{MMTV}$ constructs. These constructs were designed to examine a potential cooperative effect of homologous TM and CT domains on Env incorporation into VLPs. The effects of the mellitin SP was therefore assessed in three different formats. Recombinant baculoviruses (rBVs) expressing all constructs were generated and confirmed to express the respective chimeric HIV-Env proteins in insect cells (FIG. 1B).

The nucleotide sequence (SEQ ID NO.: 34) and amino acid sequence of the polypeptide sequence encoded therein (SEQ ID NO.: 35) are illustrated in FIGS. 9 and 10 respectively, while FIG. 11 illustrates a map of the construct.

Example 9

Effects of the Signal Peptide on Chimeric Env Expression and CD4-Binding

The effects of the mellitin SP on the total Env synthesis and cell surface expression levels of chimeric Env were measured by radioactive metabolic labeling followed by surface labeling and immunoprecipitation. When rBVs containing chimeric genes were used to infect Sf9 insect cells, all three chimeric Env proteins with the mellitin SP substitution were expressed more efficiently in Sf9 cells (M, M-CT$_{MMTV}$ and M-TM.CT$_{MMTV}$ in FIG. 1B), compared with their corresponding counterparts with the natural HIV SP (H, H-CT$_{MMTV}$ and H-TM.CT$_{MMTV}$ in FIG. 1B). FIG. 1C compares the cell surface expression levels of the constructs, and FIG. 1D shows the relative quantities of bands in FIGS. 1B and 1C by phosphorImager analysis. An enhancement by the mellitin SP substitution on the total expression of Env was observed in all constructs, independent of changes in the CT or TM-CT domains. The chimeric Env without CT showed the highest level of total expression in Sf9 cells; however, the CT-deleted M and M-TM.CT$_{MMTV}$ showed similar surface expression levels. Comparison of cell surface vs total expression levels indicated that M-TM.CT$_{MMTV}$ was the construct most efficiently transported to the cell surface as shown in FIG. 1C.

Env CD4-binding capability was also measured to examine whether the glycoprotein expressed on the cell surface was folded correctly. As shown in FIG. 2, all chimeric Env proteins with the mellitin SP exhibited higher CD4-binding compared to their corresponding constructs with the HIV SP (M vs H, M-CT$_{MMTV}$ vs H-CT$_{MMTV}$ and M-TM.CT$_{MMTV}$ vs H-TM.CT$_{MMTV}$ in FIG. 2). The mellitin SP chimera with a MMTV TM-CT substitution exhibited the highest CD4-binding level (M-TM.CT$_{MMTV}$ in FIG. 2). We observed a similar pattern when the cell surface expression (FIG. 1D) and the CD4-binding were compared suggesting that the cell surface expressed Env is folded into a correct conformation, at least for the CD4-binding domain.

Example 10

Effects of SP Substitution on Env Incorporation into VLPs

Since the chimeric Env proteins with mellitin SP substitution were expressed efficiently in Sf9 cells and exhibited higher surface expression, we determined whether these proteins could be incorporated more efficiently into VLPs containing the HIV-1 Gag protein. As shown in FIG. 3A, when 2 µg of VLPs were analyzed by Western blot, we observed that the CT-deleted mellitin SP chimeric Env (M in FIG. 3A) was incorporated at levels 3-fold higher than the corresponding construct with the original HIV SP (H in FIG. 3A). Substitution of the MMTV CT or TM-CT also was found to enhance Env incorporation (M-CT$_{MMTV}$ and M-TM.CT$_{MMTV}$ in FIG. 3A). For more detailed comparison, different amounts of H and M VLPs were resolved and compared by western blot with known levels of HIV-1 SF162 gp120. As shown in FIG. 3C, M Env incorporation was 2- to 3-fold higher than H Env (2, 1 and 0.5 µg of M vs 2, 1 and 0.5 µg of H).

Considering that the mellitin SP is a heterologous sequence and a conformational constraint may occur when fused to Con-S surface domain, the initial M construct had a flexible linker, DPINMT GS, between mellitin SP and Con-S surface domain (FIG. 1A). To evaluate the role of this linker, a chimeric Env gene, M(ΔL1) in FIG. 4B, was constructed in which the flexible linker was deleted. The deletion of the flexible linker sequence resulted in a slight decrease of Env incorporation (2, 1 and 0.5 µg of M(ΔL1) vs those of M in FIG. 3C). Also, because HIV Env expression was analyzed using BV-infected insect cells, the effects of BV gp64 and chitinase SP sequences were tested. Chimeric HIV Env constructs containing these SP substitutions did not show improvements in levels of Env incorporated into VLPs compared to the WT HIV SP (data not shown).

Example 11

Effects of the MMTV TM and CT Sequences on Env Incorporation into VLPs

Figure 4A:
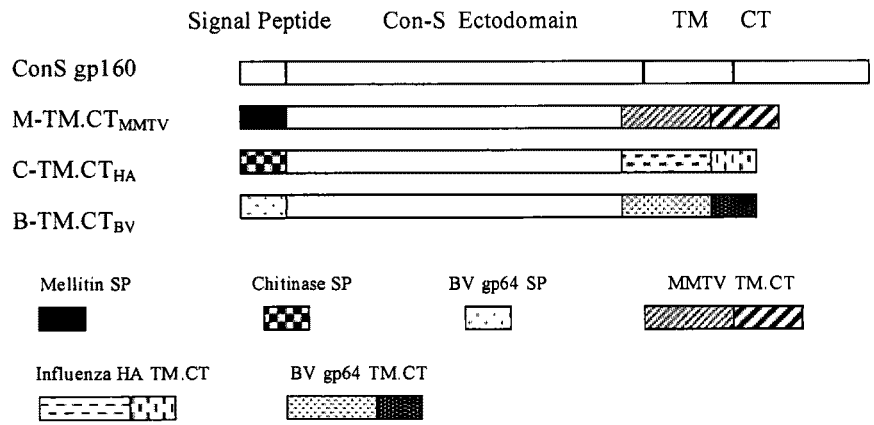
FIG. 4A: Schematic diagram of additional chimeric HIV-1 Con-S Env constructs. B-TM.CT$_{BV}$, Con-S ΔCFI with SP and TM-CT domains derived from BV SP64; C-TM.CT$_{HA}$, ConS ΔCFI with chitinase SP and influenza HA TM-CT domains.

To elucidate the role of MMTV TM and CT domains in incorporation of chimeric HIV-1 Env into VLPs, the mellitin SP based constructs were fused with the MMTV CT (M-CT$_{MMTV}$) or with MMTV TM-CT (M-TM.CT$_{MMTV}$) as shown in FIG. 1A. For quantitative comparison, different amounts of VLPs were subjected to western blot (FIG. 4A). As a standard for purified HIV-1 Env, varying amounts of HIV-1 SF162 gp120 (12.5 ng to 200 ng) were used. This comparison clearly shows that M-CT$_{MMTV}$ is incorporated into VLPs more efficiently than the M construct (FIG. 4A). The M-TM.CT$_{MMTV}$ construct containing both MMTV TM and CT showed the highest levels of Env incorporation into VLPs.

Figure 4B:
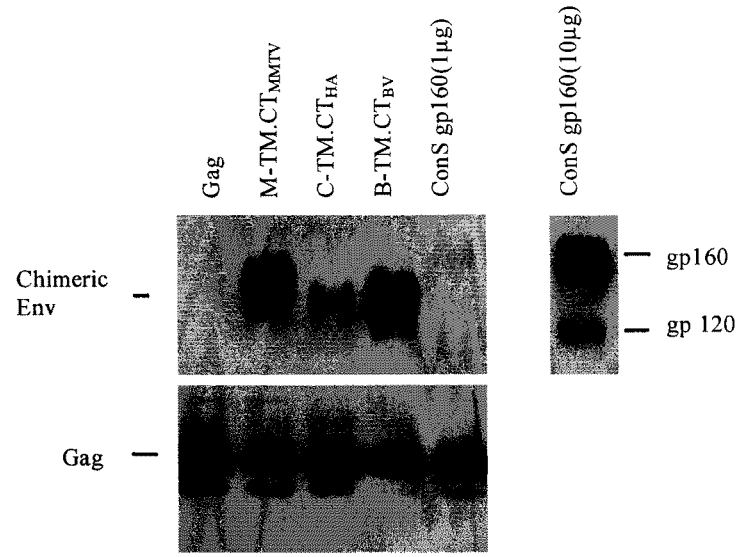
FIG. 4B: in the left panel, one microgram of M-TM.CT$_{MMTV}$, C-TM.CT$_{HA}$, B-TM.CT$_{BV}$, ConS gp160 and HIV-1 Gag VLPs were analyzed by Western blot; In the right panel, 10 μg of ConS gp160 VLP was loaded for the Western blot.
Figure 7A:
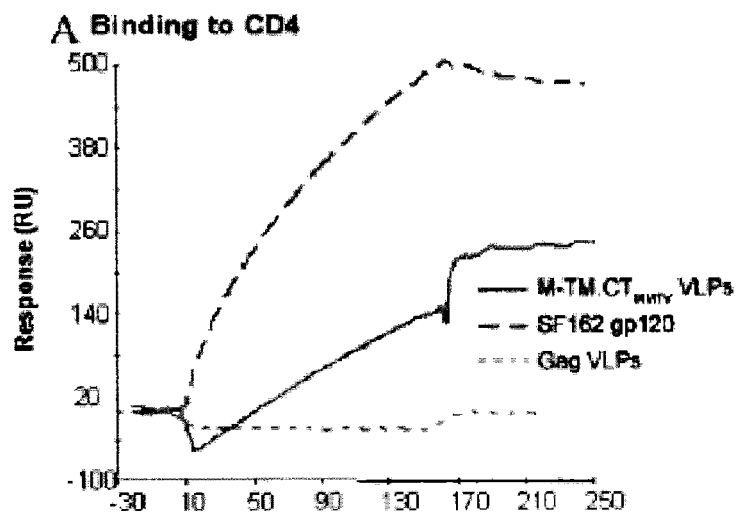
(FIGS. 7A and 7B) M-TM. CTMMTV VLPs binding to CD4 or T8 MAb, respectively.
Figure 7B:
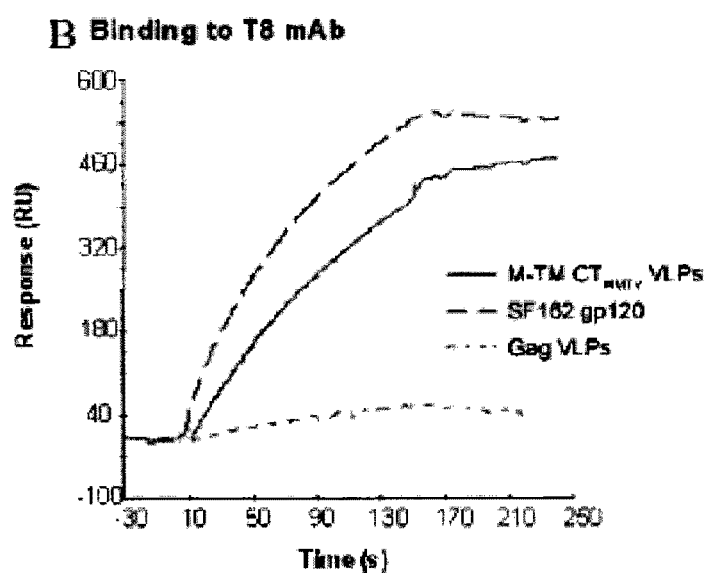
Figure 7C:
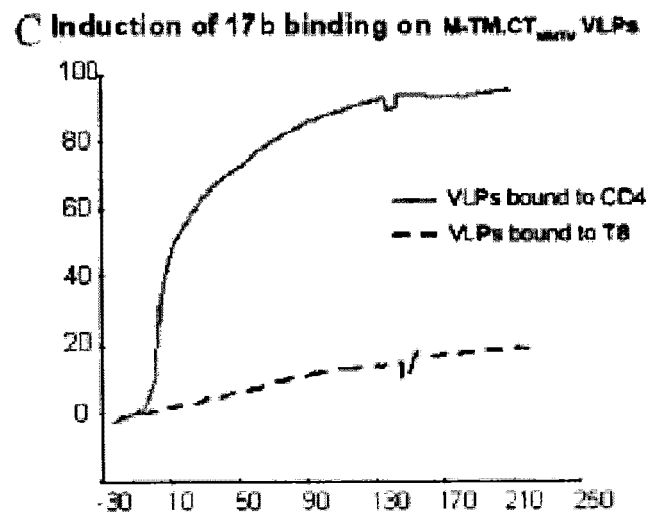
FIG. 7C: MAb 17b binding to M-TM.CTMMTV after CD4 or T8 binding.
Figure 7D:
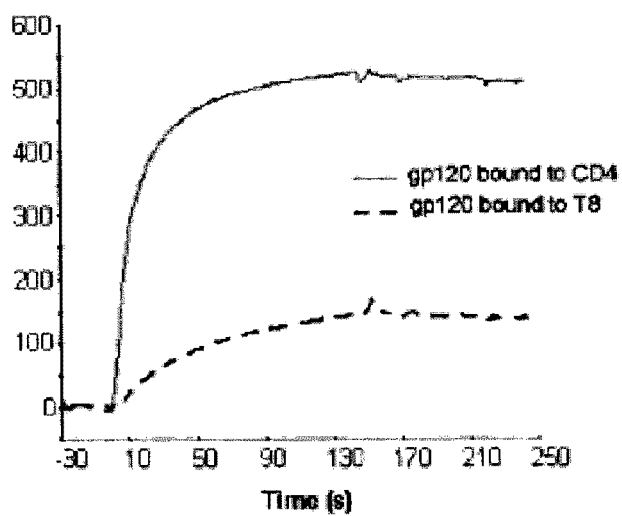
FIG. 7D: MAb 17b binding to SF162 gp120 after CD4 or T8 binding.
Figure 7E:
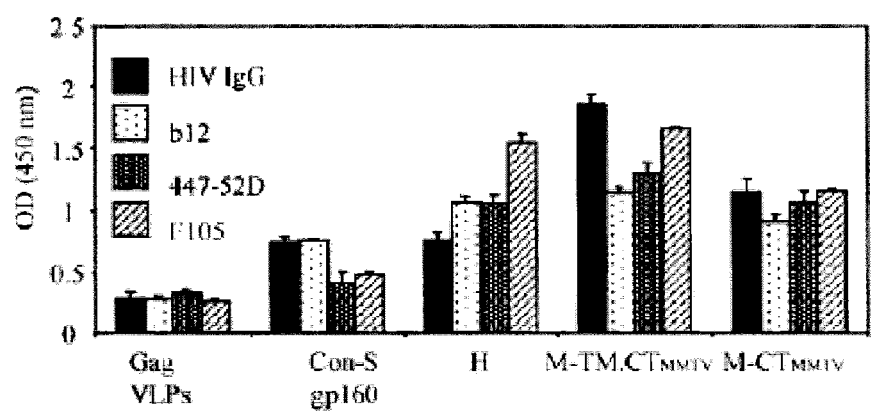
FIG. 7E: Binding of neutralizing antibodies to chimeric VLPs. Normalized VLPs (amount 0.05 μg of VLPs) were diluted to 100 μl and captured with anti-gp120 antibody-coated plates. Subsequently, Env-specific antibodies were applied, and binding was assayed by ELISA. HIV IgG, polyclonal IgG from HIV-infected patients; B12 and F105, MAbs recognizing CD4 binding site; 447-52D, MAb recognizing V3-loop. Goat anti-human IgG-HRP was used for detection. Representative data are shown from three independent experiments. Error bars represent the standard error.

We also investigated the effects of different lengths of the MMTV CT domain on incorporating Env into VLPs. A 6-amino acid (PRVSYT) truncated MMTV CT construct (M-CT$_{MMTVt}$ and M-TM.CT$_{MMTVt}$ in FIG. 4B) was examined and found to have similar levels of Env in VLPs to those with the full length MMTV CT (data not shown). The presence or absence of linkers between the junctions of HIV Env and MMTV CT or TM-CT was also compared to determine whether the presence of the linker would affect Env incorporation into VLPs. We did not observe differences in levels of Env incorporated into VLPs produced using the constructs containing a one-aa linker (D) between HIV TM and MMTV CT (H-(L2)CT and M-(L2)CT in FIG. 4B) or a two-aa (EF)

linker between the junctions of HIV Env and MMTV TM (M-(L)TM.CT, H-(L)TM.CT in FIG. 4B) (data not shown).

Example 12

Comparison of Other Chimeric HIV Envs with Heterologous TM-CT Domains

We further explored Env incorporation into VLPs with constructs having TM-CT domains derived from either influenza virus hemagglutinin (HA) or BV gp64 proteins. As diagrammed in FIG. 5A, one construct was generated to have chitinase SP and HA TM-CT (C-TM.CT$_{HA}$), and another contained the BV gp64 SP and TM-CT (B-TM.CT$_{BV}$). The incorporation of these chimeric Env into VLPs was compared with that of M-TM.CT$_{MMTV}$. The results in FIG. 5B demonstrated that all three of the chimeric constructs were found to be incorporated into VLPs at high levels, although the level of C-TM.CT$_{HA}$ was lower compared to the other two constructs. In contrast, the full-length ConS gp160 was found to be incorporated into VLP at very low levels under in the same conditions. The ConS gp160 VLP did not show detectable Env unless a ten-fold higher quantity of VLPs was loaded for Western blot analysis as shown in FIG. 5B. The data in Table 2 show that the Gag/Env molar ratios of MMTV, HA and BV derived chimeric Env VLPs were 4.0, 10.8 and 4.6, respectively. The ratio for full-length Con-S gp160 VLP was 55.7, demonstrating that the level of TM and CT domains have important roles in the incorporation of Env into VLPs.

Figure 6:
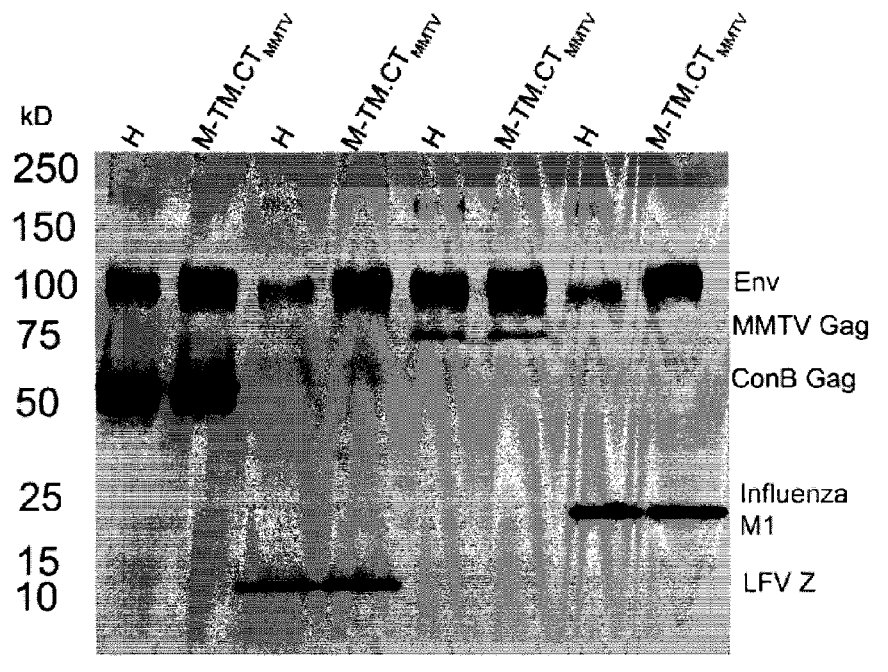

We also constructed rBVs expressing two chimeric Env proteins, H-CT$_{LFV}$ and H-TM.CT$_{LFV}$ as shown in FIG. 6A. Compared with H-CT$_{MMTV}$ and H-TM.CT$_{MMTV}$, H-CT$_{LFV}$ and H-TM.CT$_{LFV}$ have a LFV GP-derived CT or TM-CT substitution, respectively. As shown in FIG. 6B, the two chimeras were expressed efficiently in Sf9 cells infected with rBV recombinants when cell lysates were analyzed by Western blot. However, when the two chimeras were used for VLP production with either the Con-B Gag or Lassa matrix (Z) protein (LFV Z), the resulting VLPs did not contain any detectable Env. As a positive control, M-TM.CT$_{MMTV}$ VLPs showed high levels of Env with either Con-B Gag or LFV Z, demonstrating that both matrix proteins function well in VLP production and Env incorporation (FIGS. 6B and 6C). Also, the wild type LFV glycoprotein is effectively incorporated into Z-derived VLPs (data not shown), indicating that the TM/CT of LFV GP are able to function in assembly of VLPs containing the LFV Z protein. This result shows that there are specific requirements involved in Env incorporation in the assembly of VLPs, which are not fulfilled by the LFV TM/CT sequences.

Example 12

Effects of Alternative Core Proteins on Incorporation of Chimeric HIV Env into VLPs To determine whether different core proteins have preferences for Env incorporation into VLPs or whether MMTV TM/CT domains preferentially interact with their cognate core protein, the levels of Env incorporated into VLPs were compared using Con-B Gag, MMTV Gag, influenza virus M1, and LFV Z as core proteins. As shown in FIG. 7, the chimeric M-TM.CT$_{MMTV}$ Env was effectively incorporated at similar levels into all VLPs produced using four different core proteins. Therefore, the chimeric Env containing the MMTV TM-CT domain did not show obvious preference for the MMTV Gag core compared to core proteins of other viruses. Interestingly, construct H that does not have a CT domain showed decreased levels of Env incorporation into VLPs derived from LFV Z or influenza virus M1 as compared to those derived from HIV or MMTV Gag. These results suggest that the interactions of Env with Z and M1 proteins during particle assembly and budding might be different from that of HIV Gag and MMTV Gag.

Example 13

Electron Microscopy of Env Enriched VLPs

Figure 8A:
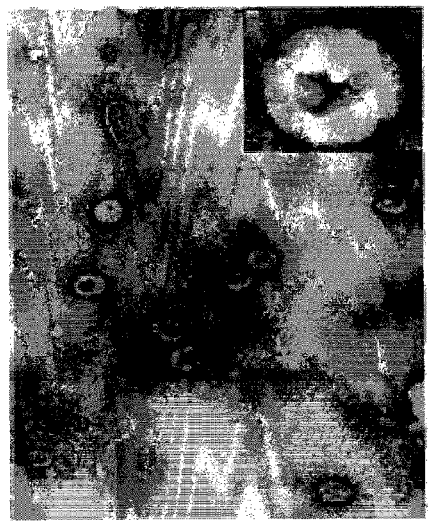
FIG. 8A: Conventional electron microscopy shows spherical VLPs negatively stained with sodium phosphotungstate with densely stained cores. Inset: 3× enlarged to show some spike projections on the surface of VLPs. Magnification: ×40,000.
Figure 8B:
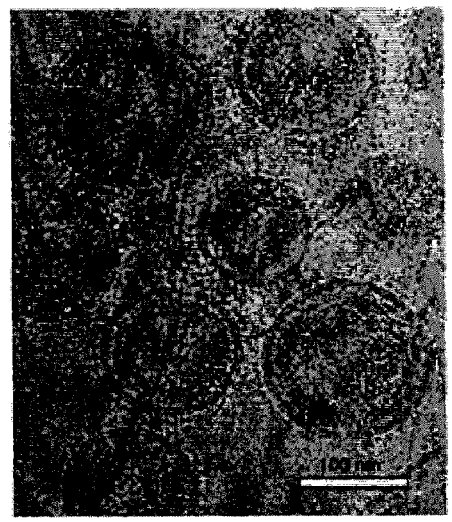
FIG. 8B: Cryo-electron microscopy shows intact structures of VLPs.
Figure 8C:
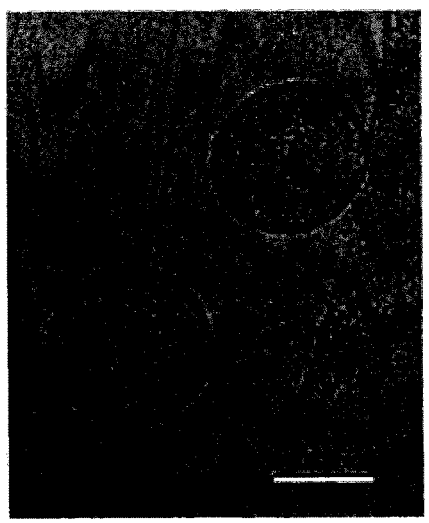
FIG. 8C: Cryo-electron microscopy image of Gag VLPs lacking Env, showing a smooth surface. Magnification, ×135,000

The structure and size of VLPs containing chimeric HIV-1 Env were examined by electron microscopy. Conventional negative staining showed roughly spherical particles with similar sizes as HIV virions (FIG. 8A). Membrane fragments were also observed, which probably resulted from disrupted particles. Although the particles are slightly deformed, Env spikes are visible in selected images as shown in the inset. Cryo-electron microscopy has the advantage of preserving the native form of VLP structures without dehydration. As shown in FIG. 8B, VLPs with chimeric HIV Env revealed intact lipid bilayers with clearly defined surface spikes. By cyro-electron microscopy, the VLPs were observed to be fairly uniform in morphology and size.

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

REFERENCES

Each of the references noted in the application are incorporated herein by reference for the corresponding discussion where the are noted.
1. Barr, P. J., K. S. Steimer, E. A. Sabin, D. Parkes, C. George-Nascimento, J. C. Stephans, M. A. Powers, A. Gyenes, G. A. Van Nest, E. T. Miller, 1987. Antigenicity and immunogenicity of domains of the human immunodeficiency virus (HIV) envelope polypeptide expressed in the yeast Saccharomyces cerevisiae. Vaccine 5:90-101.
2. Bhattacharya, J., P. J. Peters, and P. R. Clapham. 2004. Human immunodeficiency virus type 1 envelope glycoproteins that lack cytoplasmic domain cysteines: impact on association with membrane lipid rafts and incorporation onto budding virus particles. J Virol 78:5500-6.
3. Chakrabarti, B. K., W. P. Kong, B. Y. Wu, Z. Y. Yang, J. Friborg, X. Ling, S. R. King, D. C. Montefiori, and G. J. Nabel. 2002. Modifications of the human immunodeficiency virus envelope glycoprotein enhance immunogenicity for genetic immunization. J. Virol. 76:5357-5368.
4. Chakrabarti, S., M. Robert-Guroff, F. Wong-Staal, R. C. Gallo, and B. Moss. 1986. Expression of the HTLV-III envelope gene by a recombinant vaccinia virus. Nature 320:535-7.
5. Chertova, E., J. W. Bess Jr, Jr., B. J. Crise, I. R. Sowder, T. M. Schaden, J. M. Hilburn, J. A. Hoxie, R. E. Benveniste, J. D. Lifson, L. E. Henderson, and L. O. Arthur. 2002. Envelope glycoprotein incorporation, not shedding of surface envelope glycoprotein (gp120/SU), Is the primary determinant of SU content of purified human immunodeficiency virus type 1 and simian immunodeficiency virus. J Virol 76:5315-25.
6. Chow, Y. H., A. Alberti, M. Mura, C. Pretto, P. Murcia, L. M. Albritton, and M. Palmarini. 2003. Transformation of rodent fibroblasts by the jaagsiekte sheep retrovirus envelope is receptor independent and does not require the surface domain. J Virol 77:6341-50.
7. Compans, R. W., H. D. Klenk, L. A. Caliguiri, and P. W. Choppin. 1970. Influenza virus proteins. I. Analysis of polypeptides of the virion and identification of spike glycoproteins. Virology 42:880-9.
8. Demirov, D. G., and E. O. Freed. 2004. Retrovirus budding. Virus Res 106:87-102.
9. Deml, L., G. Kratochwil, N. Osterrieder, R. Knuchel, H. Wolf, and R. Wagner. 1997. Increased incorporation of chimeric human immunodeficiency virus type 1 gp120 proteins into Pr55gag virus-like particles by an Epstein-Barr virus gp220/350-derived transmembrane domain. Virology 235:10-25.
10. Desrosiers, R. C. 1999. Strategies used by human immunodeficiency virus that allow persistent viral replication. Nat Med 5:723-5.
11. Freed, E. O. 2002. Viral late domains. J Virol 76:4679-87.
12. Henriksson, P., T. Pfeiffer, H. Zentgraf, A. Alke, and V. Bosch. 1999. Incorporation of wild-type and C-terminally truncated human epidermal growth factor receptor into human immunodeficiency virus-like particles: insight into the processes governing glycoprotein incorporation into retroviral particles. J Virol 73:9294-302.
13. Ho, S. N., H. D. Hunt, R. M. Horton, J. K. Pullen, and L. R. Pease. 1989. Site-directed mutagenesis by overlap extension using the polymerase chain reaction. Gene 77:51-59.
14. Hook, L. M., Y. Agafonova, S. R. Ross, S. J. Turner, and T. V. Golovkina. 2000. Genetics of mouse mammary tumor virus-induced mammary tumors: linkage of tumor induction to the gag gene. J Virol 74:8876-83.
15. Hu, S. I., S. G. Kosowski, and K. F. Schaaf. 1987. Expression of envelope glycoproteins of human immunodeficiency virus by an insect virus vector. J Virol 61:3617-20.
16. Kang, S. M., F. S. Quan, C. Huang, L. Guo, L. Ye, C. Yang, and R. W. Compans. 2005. Modified HIV envelope proteins with enhanced binding to neutralizing monoclonal antibodies. Virology 331:20-32.
17. Kieny, M. P., Rautmann, G., Schmitt, D., Dott, K., Wain-Hobson, S., Alizon, M., Girard, M., Chamaret, S., Laurent, A., Montagnier, L., Lecocq, J.-P. 1986. AIDS virus env protein expressed from a recombinant vaccinia virus. Biotechnology (NY) 4:790-795.
18. Lasky, L. A., J. E. Groopman, C. W. Fennie, P. M. Benz, D. J. Capon, D. J. Dowbenko, G. R. Nakamura, W. M. Nunes, M. E. Renz, and P. W. Berman. 1986. Neutralization of the AIDS retrovirus by antibodies to a recombinant envelope glycoprotein. Science 233:209-12.
19. Li, Y., J. J. Bergeron, L. Luo, W. J. Ou, D. Y. Thomas, and C. Y. Kang. 1996. Effects of inefficient cleavage of the signal sequence of HIV-1 gp 120 on its association with calnexin, folding, and intracellular transport. Proc Natl Acad Sci USA 93:9606-11.
20. Li, Y., L. Luo, D. Y. Thomas, and C. Y. Kang. 1994. Control of expression, glycosylation, and secretion of HIV-1 gp120 by homologous and heterologous signal sequences. Virology 204:266-78.
21. Liao, H. X., L. L. Sutherland, S. M. Xia, M. E. Brock, R. M. Scearce, S. Vanleeuwen, S. M. Alam, M. McAdams, E. A. Weaver, Z. Camacho, B. J. Ma, Y. Li, J. M. Decker, G. J. Nabel, D. C. Montefiori, B. H. Hahn, B. T. Korber, F. Gao, and B. F. Haynes. 2006. A group M consensus envelope glycoprotein induces antibodies that neutralize subsets of subtype B and C HIV-1 primary viruses. Virology 353:268-82.
22. Lopez-Verges, S., G. Camus, G. Blot, R. Beauvoir, R. Benarous, and C. Berlioz-Torrent. 2006. Tail-interacting protein TIP47 is a connector between Gag and Env and is required for Env incorporation into HIV-1 virions. Proc Natl Acad Sci USA 103:14947-52.
23. Perez, M., D. L. Greenwald, and J. C. de la Torre. 2004. Myristoylation of the RING finger Z protein is essential for arenavirus budding. J Virol 78:11443-8.
24. Provitera, P., R. El-Maghrabi, and S. Scarlata. 2006. The effect of HIV-1 Gag myristoylation on membrane binding. Biophys Chem 119:23-32.
25. Raghuraman, H., and A. Chattopadhyay. 2004. Interaction of melittin with membrane cholesterol: a fluorescence approach. Biophys J 87:2419-32.
26. Roberts, P. C., R. A. Lamb, and R. W. Compans. 1998. The M1 and M2 proteins of influenza A virus are important determinants in filamentous particle formation. Virology 240:127-37.
27. Rousso, I., M. B. Mixon, B. K. Chen, and P. S. Kim. 2000. Palmitoylation of the HIV-1 envelope glycoprotein is critical for viral infectivity. Proc Natl Acad Sci USA 97:13523-5.
28. Rusche, J. R., D. L. Lynn, M. Robert-Guroff, A. J. Langlois, H. K. Lyerly, H. Carson, K. Krohn, A. Ranki, R. C. Gallo, D. P. Bolognesi, and 1987. Humoral immune response to the entire human immunodeficiency virus envelope glycoprotein made in insect cells. Proc. Natl. Acad. Sci. U.S.A 84:6924-6928.
29. Saifuddin, M., T. Hedayati, J. P. Atkinson, M. H. Holguin, C. J. Parker, and G. T. Spear. 1997. Human immunodeficiency virus type 1 incorporates both glycosyl phosphatidylinositol-anchored CD55 and CD59 and integral membrane CD46 at levels that protect from complement-mediated destruction. J Gen Virol 78 (Pt 8):1907-11.
30. Takefman, D. M., B. L. Sullivan, B. E. Sha, and G. T. Spear. 1998. Mechanisms of resistance of HIV-1 primary isolates to complement-mediated lysis. Virology 246:370-8.
31. Vzorov, A. N., and R. W. Compans. 2000. Effect of the cytoplasmic domain of the simian immunodeficiency virus envelope protein on incorporation of heterologous envelope proteins and sensitivity to neutralization. J Virol 74:8219-25.
32. Wyma, D. J., A. Kotov, and C. Aiken. 2000. Evidence for a stable interaction of gp41 with Pr55(Gag) in immature human immunodeficiency virus type 1 particles. J Virol 74:9381-7.
33. Yagi, M. J., and R. W. Compans. 1977. Structural components of mouse mammary tumor virus. I. Polypeptides of the virion. Virology 76:751-66.
34. Yamshchikov, G. V., G. D. Ritter, M. Vey, and R. W. Compans. 1995. Assembly of SIV virus-like particles containing envelope proteins using a baculovirus expression system. Virology 214:50-8.
35. Yang, C., and R. W. Compans. 1996. Palmitoylation of the murine leukemia virus envelope glycoprotein transmembrane subunits. Virology 221:87-97.
36. Yao, Q., F. M. Kuhlmann, R. Eller, R. W. Compans, and C. Chen. 2000. Production and characterization of simian—human immunodeficiency virus-like particles. AIDS Res Hum Retroviruses 16:227-36.

37. Ye, L., Z. Bu, A. Vzorov, D. Taylor, R. W. Compans, and C. Yang. 2004. Surface stability and immunogenicity of the human immunodeficiency virus envelope glycoprotein: role of the cytoplasmic domain. J Virol 78:13409-19.

38. York, J., and J. H. Nunberg. 2004. Role of hydrophobic residues in the central ectodomain of gp41 in maintaining the association between human immunodeficiency virus type 1 envelope glycoprotein subunits gp120 and gp41. J Virol 78:4921-6.

39. Yuste, E., W. Johnson, G. N. Pavlakis, and R. C. Desrosiers. 2005. Virion envelope content, infectivity, and neutralization sensitivity of simian immunodeficiency virus. J Virol 79:12455-63.

40. Zingler, K., and D. R. Littman. 1993. Truncation of the cytoplasmic domain of the simian immunodeficiency virus envelope glycoprotein increases env incorporation into particles and fusogenicity and infectivity. J Virol 67:2824-31.

We claim:

1. A virus-like particle comprising a chimeric human immunodeficiency virus (HIV)-Env polypeptide comprising a mouse mammary tumor virus (MMTV) transmembrane domain and cytoplasmic tail.

2. The virus-like particle of claim 1, wherein the shell of the virus-like particle comprises 2% to 50% of chimeric HIV-Env polypeptide.

3. The virus-like particle of claim 1, wherein the virus-like particle has Env-specific epitopes exposed on the outer surface thereof.

4. The virus-like particle of claim 1, wherein the Env-specific epitopes exposed on the outer surface of the virus-like particle may specifically bind with an anti-HIV-Env specific antibody.

5. A virus-like particle comprising a chimeric human immunodeficiency virus (HIV)-Env polypeptide wherein the virus-like particle is produced by cotransfecting a eukaryotic host cell with a first expression vector and a second expression vector, wherein the first expression vector expresses an HIV-1 gag polypeptide, and wherein the second expression vector expresses a chimeric HIV-Env polypeptide, the second expression vector comprising an expression promoter operably linked to a recombinant nucleic acid encoding, wherein the recombinant nucleic acid comprises a first domain encoding a heterologous signal peptide, wherein the first domain is operably linked to a second domain encoding an HIV-Env polypeptide region, and a third domain encoding a polypeptide region selected from the group consisting of a heterologous transmembrane region, a heterologous cytoplasmic tail region, and a combination of a heterologous transmembrane region and a heterologous cytoplasmic tail region wherein the third domain encodes a polypeptide comprising one of the amino acid sequences SEQ ID NOs.: 2 and 7; and allowing the cotransfected host cell to form the virus-like particles.

6. The virus-like particle of claim 5, wherein the virus-like particles are isolated by centrifugation.

7. The virus-like particle of claim 5, wherein the first domain of the second expression vector encodes a signal peptide derived from honeybee mellitin.

8. The virus-like particle of claim 7, wherein the signal peptide derived from honeybee mellitin has the amino acid sequence according to SEQ ID NO.: 31.

9. The virus-like particle of claim 5, wherein the second domain of the second expression vector encodes the chimeric HIV-1 Con-S ΔCFI Env polypeptide.

10. The virus-like particle of claim 5, wherein the amino acid sequence of the heterologous transmembrane region is selected from one of the sequences according to SEQ ID NOs.: 1-5.

11. The virus-like particle of claim 5, wherein the amino acid sequence of the heterologous cytoplasmic tail region is selected from one of the sequences according to SEQ ID NOs.: 6-11.

12. The virus-like particle of claim 5, wherein the chimeric HIV-Env polypeptide comprises the amino acid sequences SEQ ID NO.: 31, the chimeric HIV-1 Con-S ΔCFI Env polypeptide, and one of SEQ ID NOs.: 2 and 7.

13. The virus-like particle of claim 5, wherein the nucleic acid sequence encoding the chimeric HIV-Env polypeptide is codon optimized for expression in an insect cell.

* * * * *